(12) United States Patent
Peluso et al.

(10) Patent No.: US 7,544,191 B2
(45) Date of Patent: Jun. 9, 2009

(54) FORMED, FILLED, SEALED SOLUTION CONTAINER, PORT AND METHOD FOR ESTABLISHING FLOW BETWEEN THE CONTAINER AND AN ADMINISTRATION SET

(75) Inventors: Francesco Peluso, Everlee (BE); Patrick Balteau, Evelette (BE); Eric Hénaut, Arquennes (BE); Barbara Mandard, Molenbeek (BE); Jean-Pierre Hartman, Rhode Saint Genèse (BE); Vincent Houwaert, Mont Saint-Aubert (BE); Giorgio Cantoni, Valdisotto (IL); Silvano Sforacchi, Grosotto (IL)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 918 days.

(21) Appl. No.: 10/277,432

(22) Filed: Oct. 22, 2002

(65) Prior Publication Data
US 2004/0078024 A1    Apr. 22, 2004

(51) Int. Cl.
*A61B 19/00* (2006.01)
*A61M 5/32* (2006.01)

(52) U.S. Cl. ............... 604/414; 604/408; 604/415; 604/416

(58) Field of Classification Search ............ 604/6.16, 604/264, 403, 408, 411, 414, 533, 200, 201, 604/204, 167.01, 167.03, 167.05, 27, 33, 604/905; 383/210.1; 222/83, 96, 104, 153.05–7, 222/548
See application file for complete search history.

(56) References Cited

U.S. PATENT DOCUMENTS

| 1,259,057 A | 3/1918 | Vick ........................... 222/83 |
| 2,073,292 A | 3/1937 | Waite et al. ................... 222/81 |
| 2,849,256 A | 8/1958 | Kowal ......................... 422/282 |

(Continued)

FOREIGN PATENT DOCUMENTS

EP          0 416 454 A2     3/1991

(Continued)

OTHER PUBLICATIONS

International Search Report for International Application No. PCT/US2006/019728 dated Oct. 26, 2006.

(Continued)

*Primary Examiner*—Leslie R Deak
(74) *Attorney, Agent, or Firm*—Ira D. Finkelstein; K & L Gates LLP

(57) ABSTRACT

A formed, filled, and sealed container, access port and method for establishing fluid flow from the container to an administrative set is provided. The container is collapsible and has an inlet and an outlet. A hollow port is sealed to the container and a perforator inside the port pierces and becomes embedded in the container. Solution in the container is withdrawn into the port. A line attached to the port and an administrative set further establishes flow between the container and the administration set. The port may be operated with a single-hand to establish fluid flow from the container to the administrative set. After the perforator is embedded in the container, a lock on the port prevents the perforator from removal from the container. Activation of the lock produces an audible and/or visible notification.

15 Claims, 16 Drawing Sheets

U.S. PATENT DOCUMENTS

| | | | | |
|---|---|---|---|---|
| 3,512,524 | A | 5/1970 | Drewe | 604/192 |
| 3,653,546 | A | 4/1972 | Hazard | 222/83 |
| 3,986,508 | A | 10/1976 | Barrington | 604/122 |
| RE29,656 | E | 6/1978 | Chittenden et al. | 604/413 |
| 4,201,208 | A | 5/1980 | Cambio, Jr. | 604/411 |
| 4,314,654 | A | 2/1982 | Gaubert | 222/83 |
| 4,322,018 | A | 3/1982 | Rutter | 222/83 |
| 4,364,387 | A * | 12/1982 | Larkin | 604/411 |
| 4,405,163 | A | 9/1983 | Voges et al. | |
| 4,416,395 | A | 11/1983 | Gaubert | 222/83 |
| 4,439,188 | A * | 3/1984 | Dennehey et al. | 604/534 |
| 4,475,566 | A | 10/1984 | Haines | 137/68.3 |
| 4,548,606 | A | 10/1985 | Larkin | 604/414 |
| 4,567,999 | A | 2/1986 | Hjertman et al. | 222/83 |
| 4,632,673 | A | 12/1986 | Tiitola et al. | |
| 4,676,775 | A | 6/1987 | Zolnierczyk et al. | |
| 4,681,243 | A | 7/1987 | Takasugi | 222/83 |
| 4,696,411 | A | 9/1987 | Graf et al. | 220/281 |
| 4,767,407 | A * | 8/1988 | Foran | 604/164.06 |
| 4,798,605 | A | 1/1989 | Steiner et al. | 604/411 |
| 5,337,775 | A | 8/1994 | Lane et al. | 137/68.29 |
| 5,603,706 | A | 2/1997 | Wyatt et al. | |
| 5,766,147 | A | 6/1998 | Sancoff et al. | |
| 5,810,398 | A | 9/1998 | Matkovich | 285/3 |
| 5,868,433 | A | 2/1999 | Matkovich | 285/3 |
| 5,895,383 | A | 4/1999 | Niedospial, Jr. | 604/403 |
| 5,960,992 | A | 10/1999 | Bernstein et al. | 222/83.5 |
| 6,068,617 | A * | 5/2000 | Richmond | 604/255 |
| 6,071,366 | A | 6/2000 | Yamada | |
| 6,082,584 | A | 7/2000 | Stern | 222/83 |
| 6,131,767 | A * | 10/2000 | Savage et al. | 222/1 |
| 6,142,446 | A | 11/2000 | Leinsing | |
| 6,161,728 | A | 12/2000 | Dark | 222/83 |
| 6,220,482 | B1 | 4/2001 | Simmel et al. | 222/83 |
| 6,223,924 | B1 | 5/2001 | Ek et al. | 220/258.4 |
| 6,253,804 | B1 | 7/2001 | Safabash | 141/97 |
| 6,258,078 | B1 | 7/2001 | Thilly | 604/411 |
| 6,279,779 | B1 | 8/2001 | Laciacera et al. | 222/83 |
| 6,280,431 | B1 | 8/2001 | Domkowski et al. | 604/411 |
| 6,293,431 | B1 | 9/2001 | Seymour et al. | 222/83 |
| 6,478,771 | B1 | 11/2002 | Lavi et al. | |
| 7,077,848 | B1 * | 7/2006 | de Juan et al. | 606/108 |
| 2001/0003996 | A1 | 6/2001 | Jansen et al. | |
| 2002/0093192 | A1 | 7/2002 | Matkovich | |
| 2002/0128628 | A1 | 9/2002 | Fathallah | |

FOREIGN PATENT DOCUMENTS

| | | |
|---|---|---|
| EP | 1060730 | 12/2000 |
| EP | 1081054 | 3/2001 |
| LU | 90268 | 8/2007 |
| WO | WO93/20772 | 10/1993 |
| WO | WO2004/037337 | 5/2004 |

OTHER PUBLICATIONS

International Search Report from corresponding PCT application, PCT/US03/32398, mailed Jun. 2, 2004.

European Search Report of EP 07015180.8 dated Sep. 20, 2007.

* cited by examiner

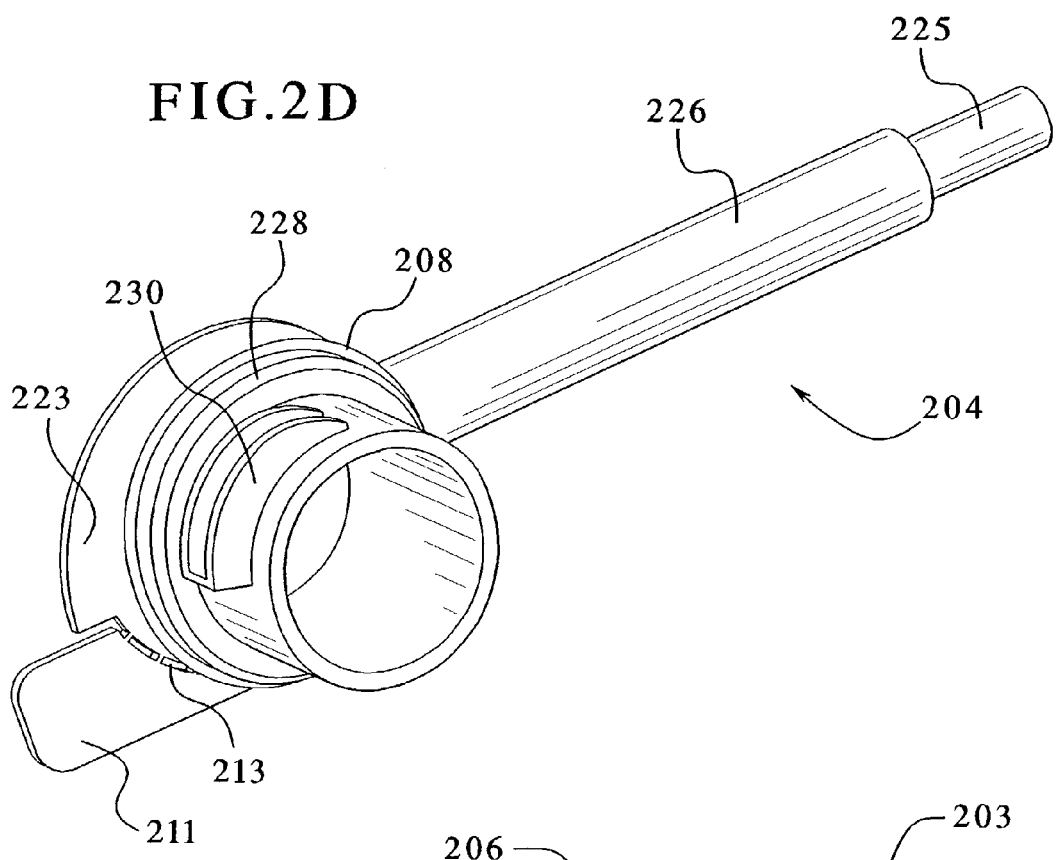
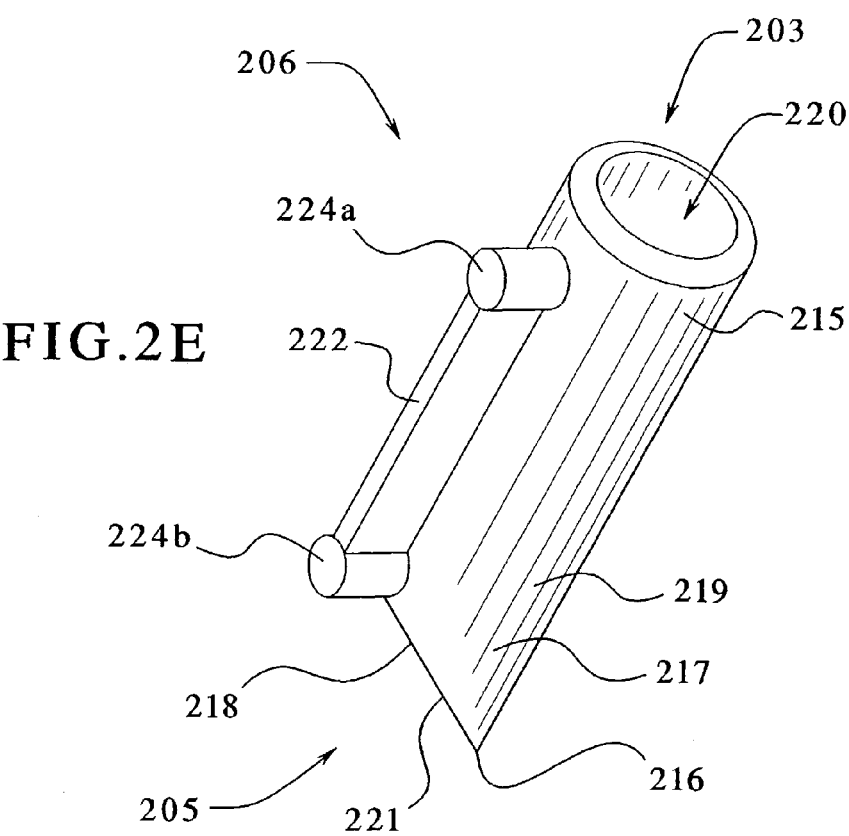

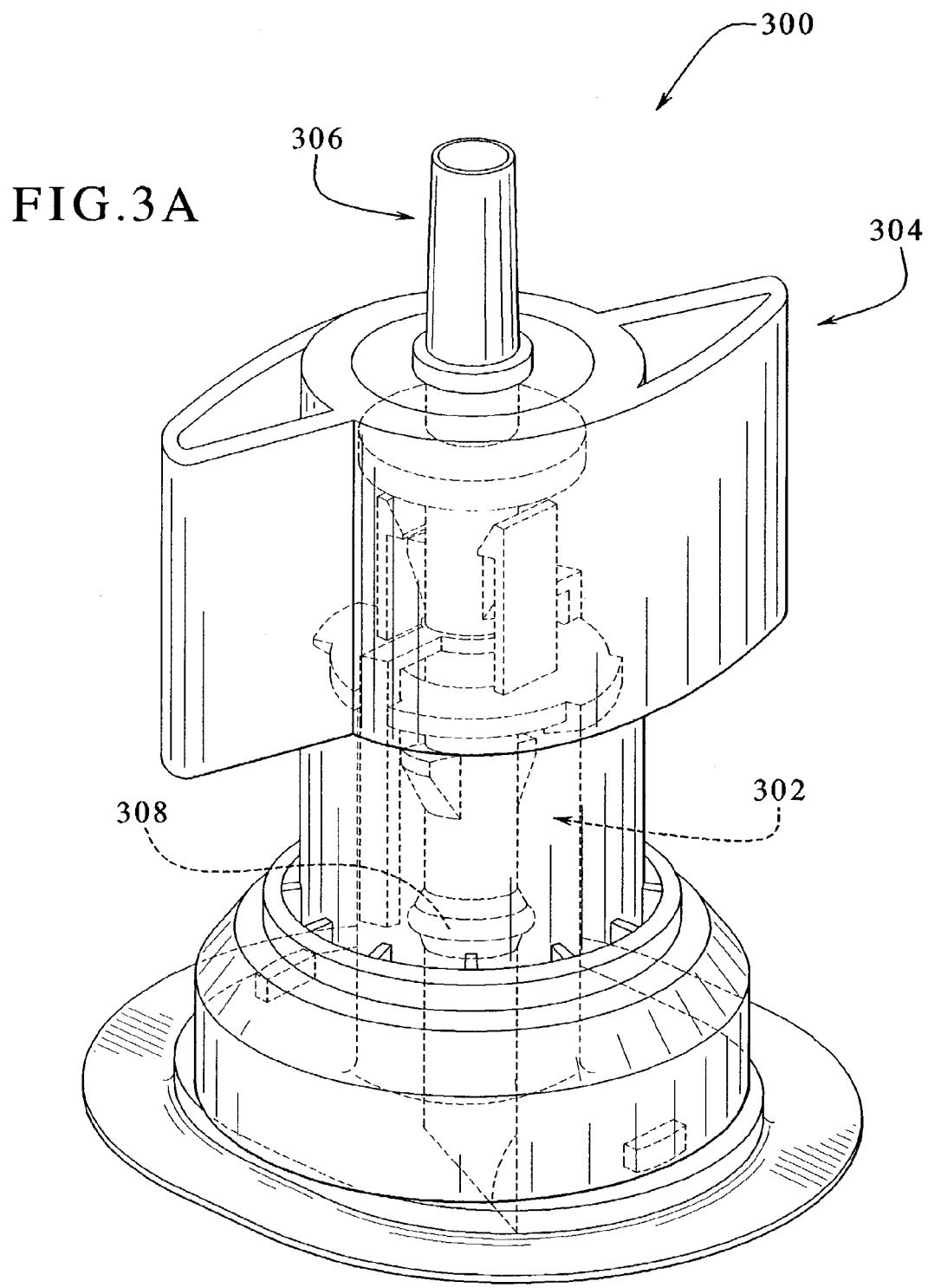

FORMED, FILLED, SEALED SOLUTION CONTAINER, PORT AND METHOD FOR ESTABLISHING FLOW BETWEEN THE CONTAINER AND AN ADMINISTRATION SET

BACKGROUND OF THE INVENTION

The present invention generally relates to a container, an access port and a method for establishing flow between the container and an administration set. The access port may establish flow of fluid from the container into an appropriate administration set. More specifically, a valve or base that seals to a container is provided. A perforator or plunger in the valve punctures the container and provides access to the solution in the container.

Containers for the administration of medical solutions are well known. Typically, the containers are made from flexible film that is folded and sealed together along peripheral side edges. Further, the containers typically have an inlet and an outlet. The containers further typically have a device for piercing the outlet and establishing a fluid communication between the device and the solution inside the container. The solution may then be exhausted from the device to an administrative set and/or patient.

Maintaining the sterility of the medical solution to be administered to the patient is extremely important. However, handling of the medical solution container may create risks of contamination. The risk of contamination may increase in emergency situations where quick manipulation on the various components may introduce bacteria or other pathogens into the container. For example, a user may inadvertently touch and/or contaminate a sterile end surface of an inlet or an outlet. The contamination may then be transferred to the contents of the container.

Further, containers for the administration of medical solutions are typically flexible. Accordingly, making a sterile connection to the flexible container for withdrawing the contents in a sterile manner may be difficult. For example, U.S. Pat. No. Re. 29,656 to Chittenden et al. discloses an additive transfer unit having a tubular member that seals to a solution container. The unit includes a needle that punctures a stopper of the solution container. Obtain a liquid-tight and leakproof connection through the flexible container using traditional medical connectors such as, for example, needles or piercing pins is difficult.

Further, administration ports are securely bonded to the flexible container. However, the administrative ports of known flexible solution containers are often the weakest part of the container. Accordingly, certain medical solutions which are sensitive to oxygen and/or other penetrating gases may be compromised. Further, pre-formed administration ports constitute potential sites of leakage and are potential points of contaminant ingress.

Other means for establishing a fluid connection between the container and an administration set are also known. Generally, known access ports require a two-handed operated access port and do not produce audible or visible notification when the access port is fully engaged. Further, many of the known access ports do not substantially protect against touch and air-borne contaminants.

A need, therefore, exists for a formed, filled, sealed solution container with an access port and a method for establishing flow between the container and an administration set. Accordingly, a medical solution container having an improved inlet and outlet port to reduce the likelihood of contamination during storage and/or use is needed. Further, a medical solution container and access port with improved ease of handling is needed. Further still, a solution container and an access port with a liquid tight seal to avoid leaking, minimize touch and/or airborne contamination and minimize permeation of oxygen and/or other gases are needed.

SUMMARY OF THE INVENTION

The present invention provides a formed, filled, sealed solution container with an access port and a method for establishing a fluid connection between the container and an administrative set. More specifically, the port is sealed to the container and has means to puncture said container. The fluid in the container is removed from the container through the port to an administrative line. The administrative line further carries the fluid to an administrative set.

The port may have a valve and a perforator. The valve may include a peripheral sealing flange or ring that may allow for sealing to the container. The valve may define a cylindrical opening that may receive and slidingly couple to a perforator or plunger. The cylindrical opening may guide the perforator or plunger to puncture the container and open access to the solution contained therein. The perforator or plunger may have a hollow shaft that includes a tri-slope bevel on the end facing the film of the container. The tri-slope bevel of the perforator or plunger punctures and tears a stretched film of the container below the sealing flange of the valve.

The present invention may provide single-handed operation and may provide audible and visible notification when the tri-slope bevel has punctured the film to allow solution flow. Further, the present invention may fully shroud the fluid generation path to exclude touch and air-borne contamination. The present invention may further reduce the amount of force needed to penetrate the film of the container. Further, the perforator or plunger of the present invention may not be removed from the fluid engagement position, after engagement is achieved.

To this end, in an embodiment of the present invention, a container is provided. The container has a film, a port and a tab. The film is folded to define sides and the sides are sealed to define an interior. The port defines an outlet through which fluid communication with the interior is established. The tab is attached to the port and the tab identifies establishment of fluid communication with the interior.

In another embodiment, the tab of the container is detached from the port after fluid communication is established.

In another embodiment, the container further has a perforator attached to the port wherein the tab is attached to the perforator and attached to the port and further wherein the tab is detached from the perforator after the fluid communication is established.

In another embodiment, the container further has a shell having a first part attached to a second part defining the tab wherein detachment of the first part from the second part identifies establishment of the fluid communication.

In another embodiment, the container further has a cock attached to the port wherein the tab is attached to the cock and further wherein the tab is removed from the cock before the fluid communication is established.

In another embodiment, identification of the establishment of fluid communication by the tab produces an audible notification.

In another embodiment, the container further has a line having a first end and a second end wherein the first end is attached to the port.

Moreover, in another embodiment of the present invention, a port for establishing fluid flow from a container to an administration set is provided. The port has a valve having a housing defining an interior, a shoulder on the housing, a cock, a catch, and a plunger. The cock is attachable to the valve and axially guided by the shoulder of the housing. The catch on the valve locks the cock and locking of the cock produces a sound. The plunger has a hollow shaft and a tip. The plunger is in the interior of the valve and rotation of the cock forces the plunger to protrude from the interior of the valve and forces the tip to penetrate the container. The tip of the plunger is locked in the container after the cock is locked.

In another embodiment, the port further has a gasket on the plunger.

In another embodiment, the port further has a removable tab on the cock wherein the tab impedes rotation of the cock.

In another embodiment, the port further has a knob associated with the plunger wherein the knob guides the plunger in the valve and further wherein the knob prevents rotation of the plunger.

In another embodiment, the port further has a peripheral foot section integrally formed with the valve wherein the peripheral foot section is sealed to the container.

Moreover, in another embodiment of the present invention, a method for establishing flow between a container and an administration set is provided. The method comprises the steps of: providing a port having a valve, cock and plunger wherein the valve has an interior for housing the cock and the plunger; attaching the port to the container; sealing the valve of the port to the container; rotating the cock so that the cock applies a force on the plunger; piercing the container with the plunger; locking the cock and the plunger in a position; and producing an audible notification upon locking the cock and the plunger in the position.

In another embodiment, the method further comprises the step of providing a gasket wherein a seal between the plunger and the valve is maintained with the gasket.

In another embodiment, the method further comprises the step of providing a tab on the cock.

In another embodiment, the method further comprises the step of removing the tab from the cock.

In another embodiment, the method further comprises the step of providing a line attachable to the cock.

In another embodiment, the method further comprises the step of embedding the plunger into the container.

In another embodiment, the method further comprises the step of locking the cock into the valve.

In another embodiment of the present invention, a port for establishing fluid flow from a container to an administration set is provided. The port has a valve having a shafts a perforator having an arm wherein the perforator is axially guided by the shaft of the valve, a cantilever beam protruding from the valve and a shell. The cantilever beam prevents the perforator from exiting the valve. The shell has a first part attached to a second part. The shell engages the valve and forces the perforator to pierce the container and the first part of the shell detaches from the second part of the shell after the perforator pierces the container.

In another embodiment, the port further has a gasket on the perforator wherein the gasket provides a seal between the perforator and the valve.

In another embodiment, the port further has a finger pad on the first part of the shell.

In another embodiment, the port further has slots on the valve to receive the arm of the perforator.

In another embodiment, the port further has a flange on the perforator to guide the perforator in the shaft of the valve.

In another embodiment, the port further has a protrusion on the valve wherein the protrusion mates with the shell.

In another embodiment, the port further has a wing on the shell wherein the shell is manipulated by applying force to the wing.

In another embodiment of the present invention, a method for establishing flow between a container with a port and an administration set is provided. The method comprises the steps of: providing a valve, a perforator, and a shell wherein the valve has an interior and the perforator is in the interior of the valve and further wherein the perforator protrudes from the valve; sealing the valve to the container; attaching the shell to the valve; forcing the perforator to pierce the container by rotation of the shell; piercing the bag with the perforator; locking the perforator in a position; and maintaining a seal between the perforator and the valve.

In another embodiment, the method further comprises the step of rotating the shell wherein rotation of the shell produces an axial stroke of the perforator.

In another embodiment, the method further comprises the step of embedding the perforator into the container.

In another embodiment, the method further comprises the step of locking the perforator into the valve.

In another embodiment of the present invention, a port for establishing fluid flow from a container to an administration set is provided. The port has a valve having a shaft, a perforator in the shaft of the valve, a beam on the perforator, and a latch on the valve. The valve seals to the container. The beam has a catch and the latch on the valve mates with the catch of the beam. The mating of the latch and the catch locks the perforator.

In an embodiment, the mating of the latch and the catch produces a sound.

In an embodiment, the port further has a line attached to the shaft of the valve.

In an embodiment, the perforator is hollow.

In an embodiment, the port further has an arm on the beam for locking the perforator in the valve.

Moreover, in an embodiment of the present invention, a method for establishing fluid flow between a container and an administration set is provided. The method comprises the steps of: providing a port having a gasket, a valve and a perforator wherein the valve has an interior and further wherein the perforator is in the interior of the valve; sealing the valve of the port to the container; applying pressure to the perforator and forcing the perforator to pierce the container.; locking the perforator and the valve in an activated position; and maintaining a seal between the perforator and the valve with the gasket.

In another embodiment, the method further comprises the step of breaking the seal between the valve and the container.

In another embodiment, the method further comprises the step of attaching a line to the valve In another embodiment, the method further comprises the step of locking the perforator in the valve so that rotation of the perforator is prevented.

In another embodiment of the present invention, a port for establishing fluid flow from a container to an administration set is provided. The port has a valve defining a shaft, a perforator in the shaft of the valve, a first wing and a second wing, a latch on the first wing and a catch on the second wing. The valve is sealed to the container and the latch locks to the catch. The first wing and the second wing are diametrically opposed and attached to the valve. Further, the first wing and the second wing contact the perforator wherein rotation of the first wing and the second wing forces the perforator to move toward the container.

In an embodiment, locking of the latch and the catch produces an audible notification.

In an embodiment, the port further has a slot on the valve wherein the slot has a lock for locking the perforator.

In another embodiment of the present invention, a method for establishing flow between a container with a port and an administration set is provided. The method comprises the steps of: providing a valve having a shaft wherein the valve is sealed to the container; providing a perforator in the shaft of the valve; rotating a first wing and a second wing toward each other wherein the first wing and the second wing are diametrically opposed and attached to the valve and further wherein the first wing and the second wing contact the perforator; piercing the container with the perforator; and locking the first wing and the second wing.

In another embodiment, the method further comprises the step of locking the perforator to the valve.

It is, therefore, an advantage of the present invention to provide a formed, filled, sealed solution container, port and method for establishing flow between the container and an administrative set that may be operated with a single hand.

Another advantage of the present invention is to provide a formed, filled, sealed solution container, port and method for establishing flow between the container and an administrative set that produces an audible notification when the access port is fully engaged.

Yet another advantage of the present invention is to provide a formed, filled, sealed solution container, port and method for establishing flow between the container and an administrative set that provides a visible notification when the access port is fully engaged.

A further advantage of the present invention is to provide a formed, filled, sealed solution container, port and method for establishing flow between the container and an administrative set wherein the access port excludes touch and air-borne contaminants.

A still further advantage of the present invention is to provide a formed, filled, sealed solution container, port and method for establishing flow between the container and an administrative set wherein the access port provides a design with an activation mode and where the position of the fingers and/or hand of the user is straightforward.

Another advantage of the present invention is to provide a formed, filled, sealed solution container, port and method for establishing flow between the container and an administrative set wherein the access port reduces the force required to access the container.

Yet another advantage of the present invention is to provide a formed, filled, sealed solution container, port and method for establishing flow between the container and an administrative set wherein a perforator may not be withdrawn from the container.

A further advantage of the present invention is to provide a formed, filled, sealed solution container, port and method for establishing flow between the container and an administrative set wherein the access port reduces the forces required to penetrate the container.

A still further advantage of the present invention is to provide a formed, filled, sealed solution container, port and method for establishing flow between the container and an administrative set wherein the access port allows for a choice of different raw materials for the perforator and the valve.

Additional features and advantages of the present invention are described in, and will be apparent from, the detailed description of the presently preferred embodiments and from the drawings.

BRIEF DESCRIPTION OF THE DRAWINGS

FIG. 2D illustrates a perspective view of a cock of an access port in an embodiment of the present invention.

FIG. 2E illustrates a perspective view of a plunger of an access port in an embodiment of the present invention.

FIG. 3A illustrates a perspective view of an access port in an embodiment of the present invention.

DETAILED DESCRIPTION OF THE PRESENTLY PREFERRED EMBODIMENTS

The present invention generally relates to a container with an access port and a method for establishing flow between the container and an administrative set. The port may seal to the container and may puncture the container to provide access to the solution in the container. The solution may be withdrawn from the container to an interior of the port wherein a line connecting the port to the administrative set may further withdraw the solution to the administrative set.

Figure 1:
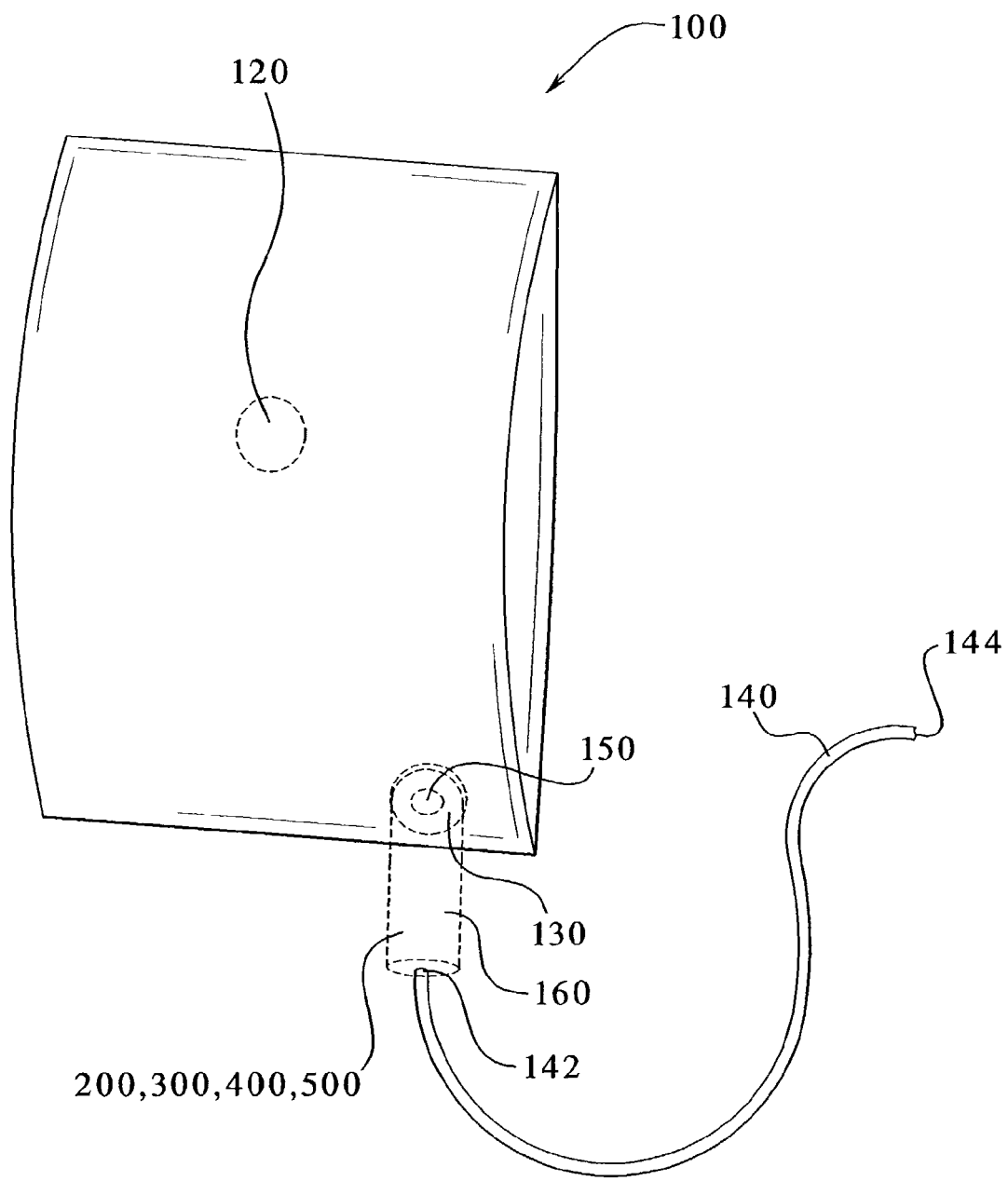
FIG. 1 illustrates a perspective view of a container with an access port in an embodiment of the present invention.

Referring now to the drawings wherein like numerals refer to like parts, FIG. 1 illustrates a container 100. The container 100 may be constructed by folding a film and sealing the film along the sides of the film. The folded film may then be filled with a medical solution and then sealed along the top to form a sealed, fluid-filled container. The container 100 may be constructed from a transparent material, such as, for example, Clearflex™. The container 100 may include solutions, such as, for example, a peritoneal dialysis solution. The container 100 may have an input 120 for receiving an additive. The input 120 may have an injection site protected by a plastic cap.

The container 100 may further have an output 130 for providing the medical solution to a patient. The output 130 may have a liner constructed from an elastomeric material, such as, for example, film 150, interposed between an end surface of the output 130 and an access port 160. The film 150, of the output 130 may be engaged by the access port 160 to establish a fluid connection between the access port 160 and the container 100. Further, an administration line 140 may connect the container 100 to an object, such as, a patient, other bag, or the like. A fluid path may be established by connecting the administration line 140 to the container 100 and the object. The administration line 140 may be connected to the container 100 by an access port 160.

Figure 2A:
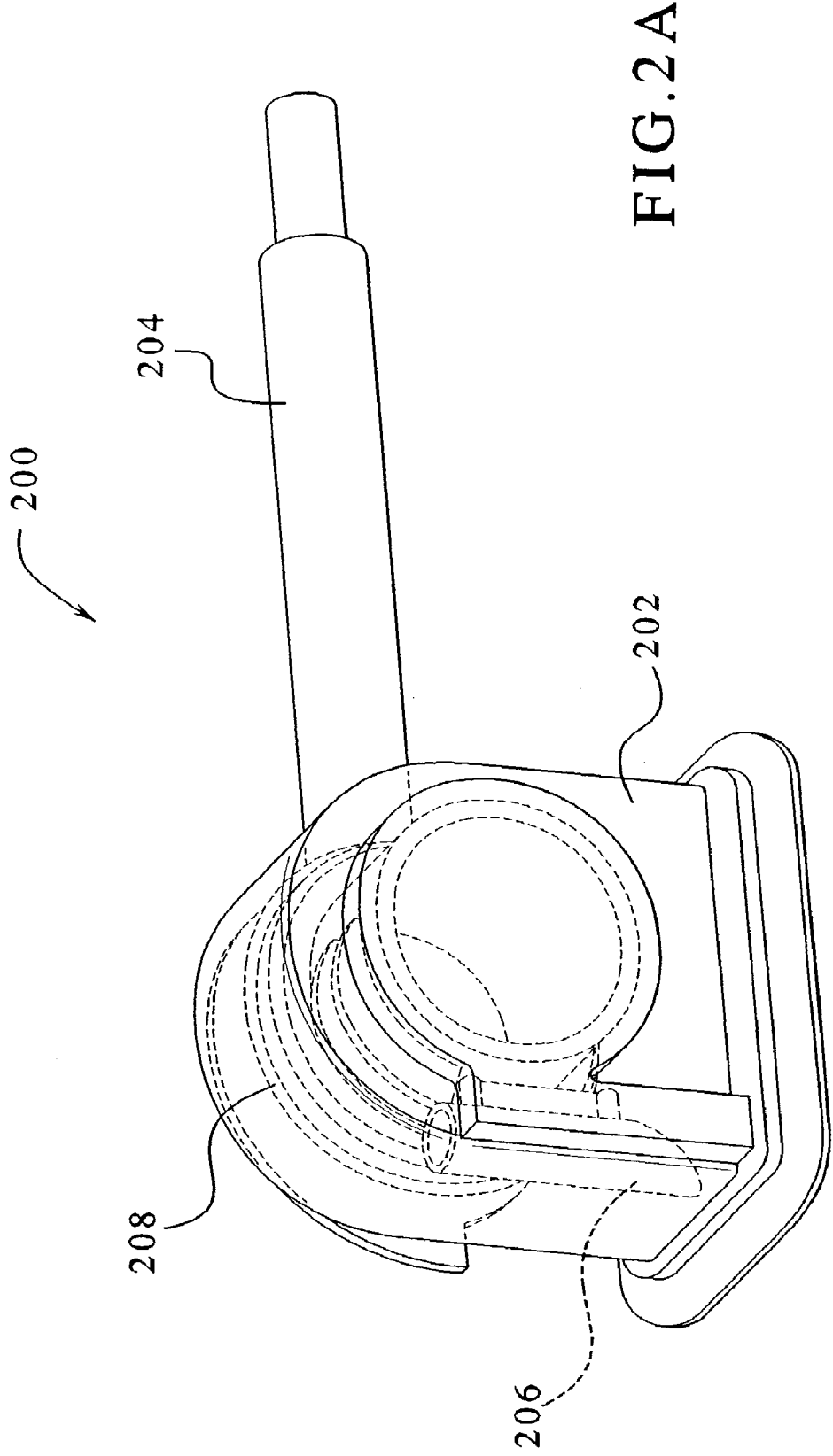
FIG. 2A illustrates a perspective view of an access port in an embodiment of the present invention.

Referring now to FIG. 2A, an access port 200 is generally illustrated. To access the solution in the container 100, the access port 200 may establish flow of fluid through the output 130 from the container 100 to the administration line 140. In an embodiment of the present invention, the access port 200 may have a valve 202, a cock 204, a plunger 206, and a gasket 208. The plunger 206 of the access port 200 is shown in a standby position.

Figure 2B:
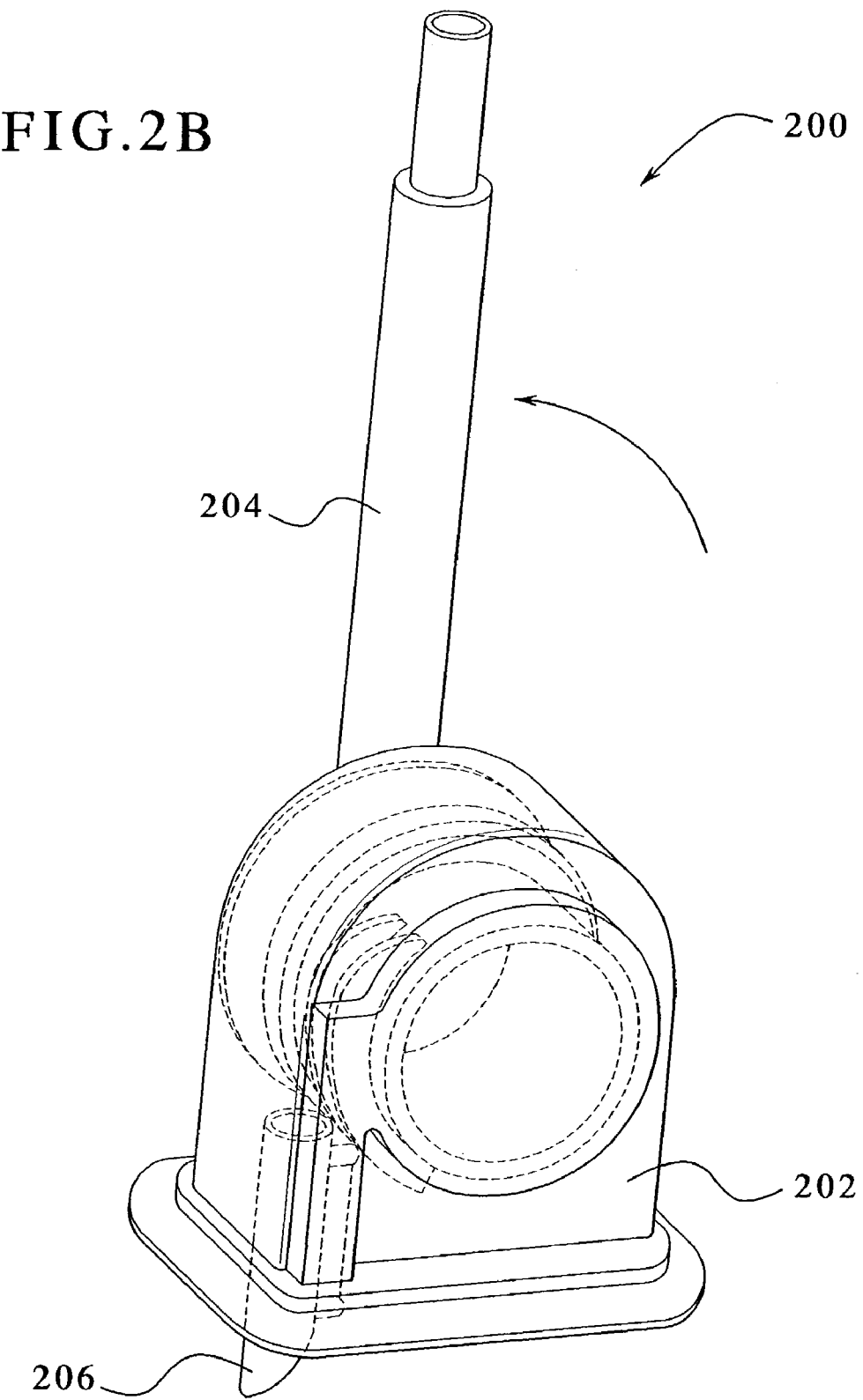
FIG. 2B illustrates a perspective view of an access port in an embodiment of the present invention.

Referring to FIG. 2B, the plunger 206 of the access port 200 is shown in an activated position. By rotating the cock 204 from a substantially horizontal position (standby position) to a substantially vertical position, the access port 200 may be activated. The rotation of the cock 204 may force the plunger 206 to lower and/or to pierce the container 100.

Figure 2C:
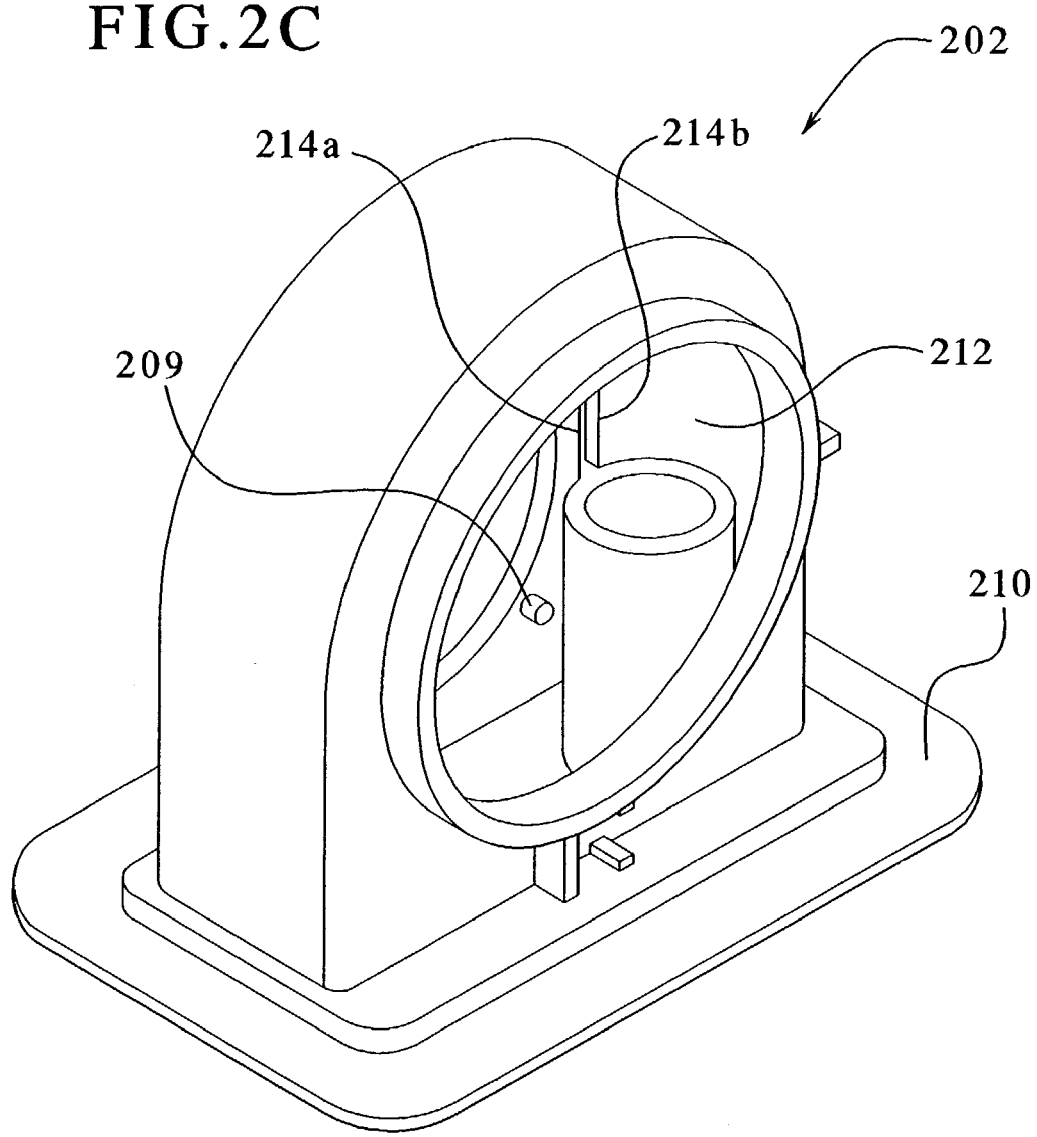
FIG. 2C illustrates a perspective view of a valve of an access port in an embodiment of the present invention.

Referring to FIG. 2C, the valve 202 may be molded from, for example, a blend that ensures a number of different functions, such as, for example, an E modulus of approximately 900 MPa. The valve 202 may be surrounded by a peripheral foot section 210 that may be sonically sealed onto the film 150 of the solution container 100. The foot section 210 may prevent leakage of the medical solution from the container 100. The valve 202 may provide a cylindrical housing 212 having two shoulders 214a and 214b. The cock 204 may be axially guided by the two shoulders 214a and 214b of the cylindrical housing 212. On an internal side of the valve 202, internal catches 209 may be designed to establish a standby position and an activated position of the plunger 206 as shown in FIGS. 2A and 2B, respectively. Preferably, locks may be provided to lock the plunger 206 in a standby or an activated position.

Referring again to FIG. 2A, the plunger 206 of the access port 200 is shown in a standby position, i.e. the cock 204 is in a substantially horizontal position, and the plunger 206 is enclosed within the valve 202. Referring to FIG. 2B, the access port 200 with the plunger 206 locked in an activated position is illustrated, i.e. the cock 204 is in a substantially vertical position, and the plunger 206 is protruding from the valve 202. Further, the valve 202 may be inclusive of a latch that may lock the cock 204 in the activated mode. Locking the cock 204 may generate a sound thereby providing an audible notification that the cock 204 has been locked.

Referring to FIG. 2E, the plunger 206 may be molded from a blend including, for example, an E modulus greater than 1500 MPa. The plunger 206 may provide at least three functions. First, the plunger 206 may puncture the film 150 of the container 100 and may open an access to the solution. A tip 216 of the plunger 206 may be designed to puncture and/or to tear the film 150 located below the peripheral foot section 210 of the valve 202. More specifically, the plunger 206 may be shaped from a hollow cylinder that tapers from a first end 203 to a second end 205 of the plunger 206. An outside surface 215 of the plunger 206 may have a first cut 217 and a second cut 219 angularly disposed to each other at the second end 205 of the plunger 206 to define the tip 216. The second end 205 with the first cut 217 and the second cut 219 define a tri-slope bevel 218 of the tip 216. Further, the design of the tri-slope bevel 218 of the tip 216 of the plunger 206 may generate minimal friction forces.

Second, the plunger 206 may allow solution flow from the container 100 into the valve 202 through a hollowed shaft 220 of the plunger 206. Third, the plunger 206 may have an axial and external beam 222 that may guide the plunger 206 into the valve 202 during activation of the access port 200. The axial and external beam 222 may have two knobs 224a and 224b. The axial and external beam 222 and the two knobs 224a and 224b may guide the plunger 206. The knobs 224a and 224b may prevent rotation of the plunger 206. Further, the knobs 224a and 224b may position the plunger 206 into both a standby position and an activated position. Preferably, locks may be provided to lock the plunger 206 in a standby or an activated position.

Referring to FIG. 2D, the cock 204 may be molded from a blend, such as, for example, E modulus at approximately 1000 MPa. The cock 204 may provide an exhaust of the valve 202 allowing fluid to be emptied from the valve 202. On a path 223 of the cock 204, a tearaway tamper proof tab 211 may impede any unintentional movement of the cock 204 to impede unintentional activation of the access port 200. The tamper proof tab 211 may impede rotation of the cock 204 to lock the plunger 206 of the access port 200 in a standby position. The tamper proof tab 211 may be constructed from the same material as the cock 204. The tamper proof tab 211 may be removably attached to the cock 204. Incisions 213 between the running path 223 of the cock 204 and the tamper proof tab 211 may provide for removal of the tamper proof tab 211 from the cock 204. Of course, the tamper proof tab 211 may be removably attached to the cock 204 by other means, such as, for example, adhesive or the like.

The cock 204 may provide four functions. First, the cock 204 may create a fluid path by connecting the administration line 140 to the container 100 as shown in FIG. 1. The cock 204 may be hollowed and may have, at one of its extremities, a press fit shaft 225 for bonding to the administration line 140. Second, the cock 204 may produce a force required to pierce the film 150 of the container 100 by providing a lever 226. A hand or finger of a user may be positioned on the lever 226. Third, the cock 204 may be used as a cam. For example, the cock 204 may activate the plunger 206 by rotation of the lever 226 from a substantially horizontal position to a substantially vertical position as shown in FIG. 2B. Fourth, the cock 204 may have a gasket groove 228 and a snapping catch 230. The gasket 208 may have a ring shape. The gasket 208 may ensure the liquid-tightness of the assembly and may prevent contaminants from entering a sterile fluid path. The snapping catch 230 may allow an assembly of the cock 204 into the valve 202 without affecting the relative degree of rotation of the cock 204.

The access port 200 is assembled after the valve 202, the plunger 206, the gasket 208 and the cock 204 may be connected. Removing the tamper proof tab 211 and rotating the cock 204 substantially ninety degrees may allow for an axial stroke of the plunger 206. After the plunger 206 is activated, or fully extended, the plunger 206 may be embedded into the body of the valve 202. After the plunger 206 is embedded into the body of the valve 202, the plunger 206 may not be removed from the container 100. Furthermore, the cock 204 may be locked into the body of the valve 202 so that rotation of the cock 204 may be prevented.

The rotation of the cock 204 may build a reactive force in the access port 200. The reactive force in the access port 200 may allow for single-handed operation. The access port 200 may enable the administration line 140 to be parallel to the sides of the container 100 in a standby position.

Referring now to FIG. 3A, in another embodiment of the present invention, an access port 300 may have four different parts, a valve 302, a threaded shell 304, a perforator 306, and a gasket 308. The perforator 306 of the access port 300 is shown in a standby position. Each of the four different parts of the access port 300 will be discussed in further detail.

Figure 3B:
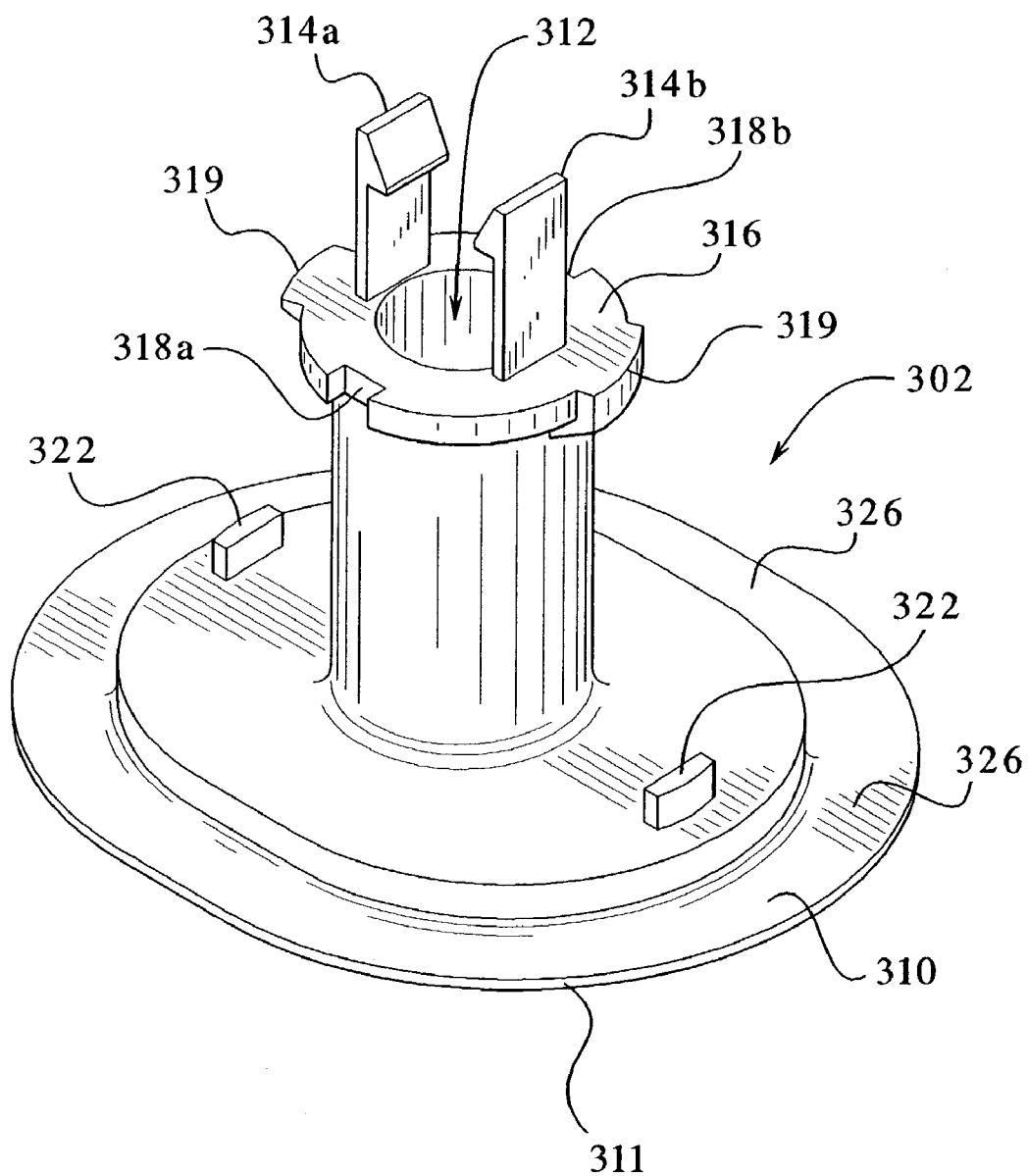
FIG. 3B illustrates a perspective view of a valve of an access port in an embodiment of the present invention.

Referring to FIG. 3B, the valve 302 may be molded from, for example, a blend of E modulus with approximately 900 MPa that provides six functions. First, the valve 302 may have an ability to seal the access port 300 onto the film 150 of the container 100. The valve 302 may be surrounded by a peripheral foot section 310. The peripheral foot section 310 may have a thickness 311 that is sonically sealed onto the film 150 of the container 100. Second, the valve 302 may allow for axial guiding of the perforator 306. The valve 302 may have a cylindrical hollow shaft 312 for the axial guiding of the perforator 306. Third, the valve 302 may position the perforator 306 in a standby position and an activated position. Two cantilever beams 314a and 314b may protrude from a top 316 of the valve 302. The two cantilever beams 314a and 314b may prevent the perforator 306 from removal from the valve 302.

Figure 3C:
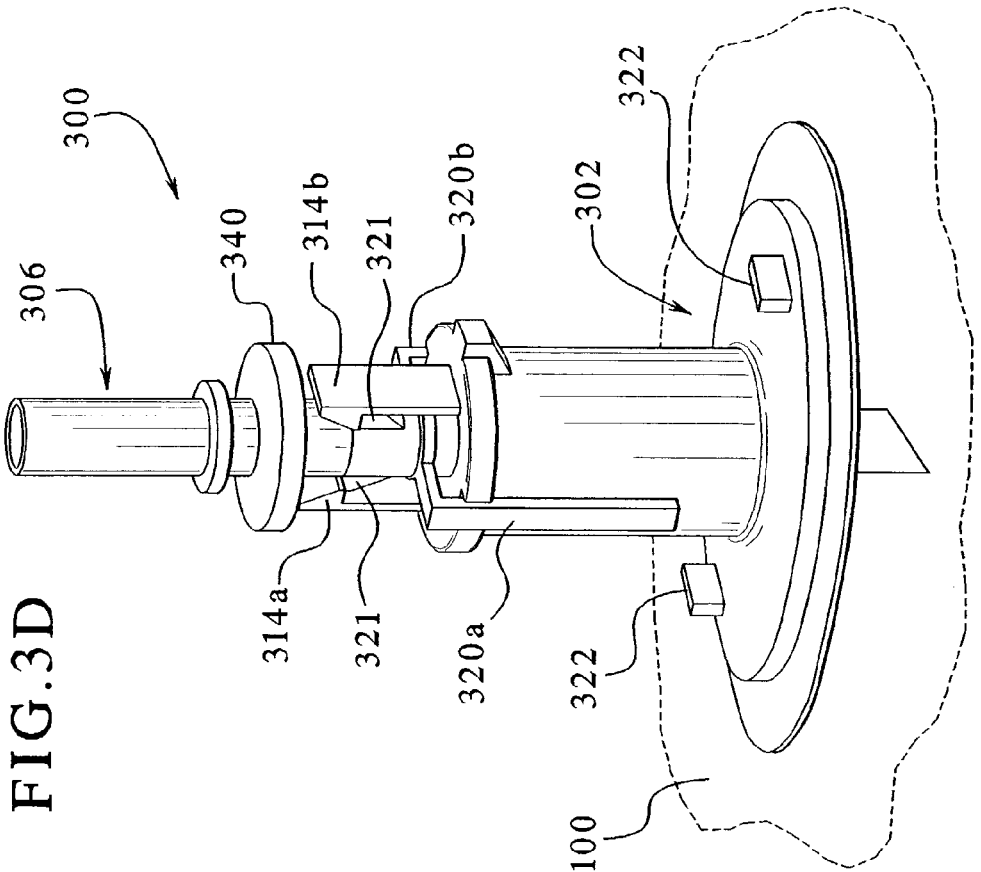
FIG. 3C illustrates a perspective view of a perforator and a valve of an access port in an embodiment of the present invention.
Figure 3D:
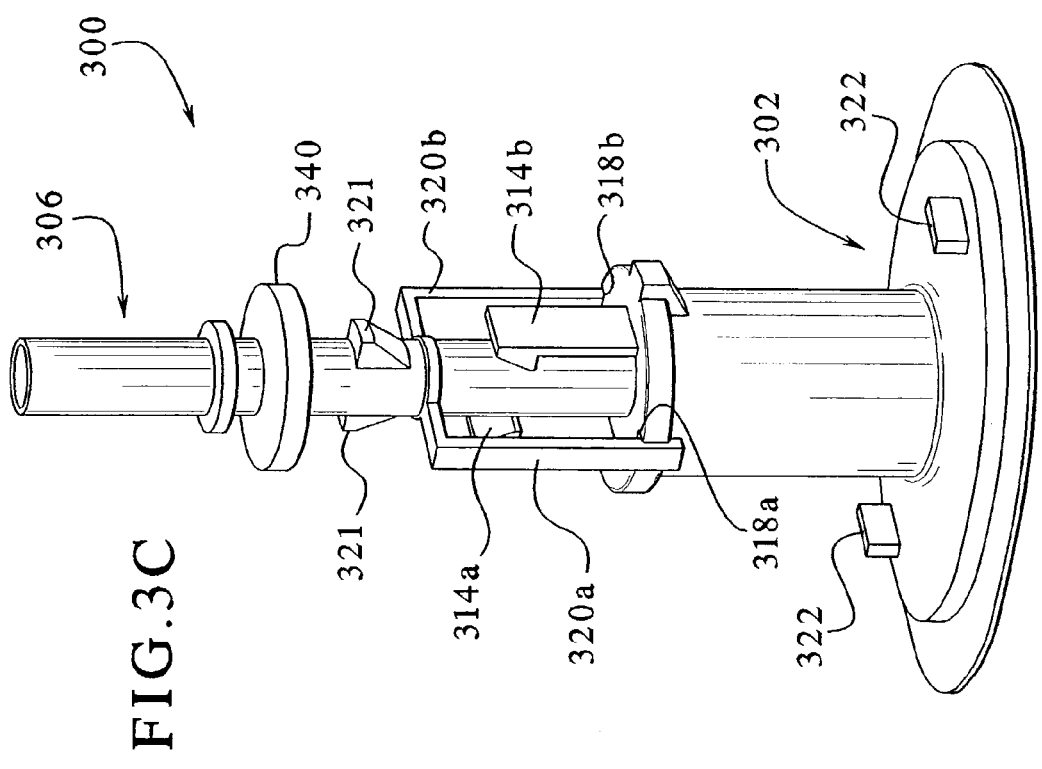
FIG. 3D illustrates a perspective view of a perforator and a valve of an access port in an embodiment of the present invention.
Figure 3E:
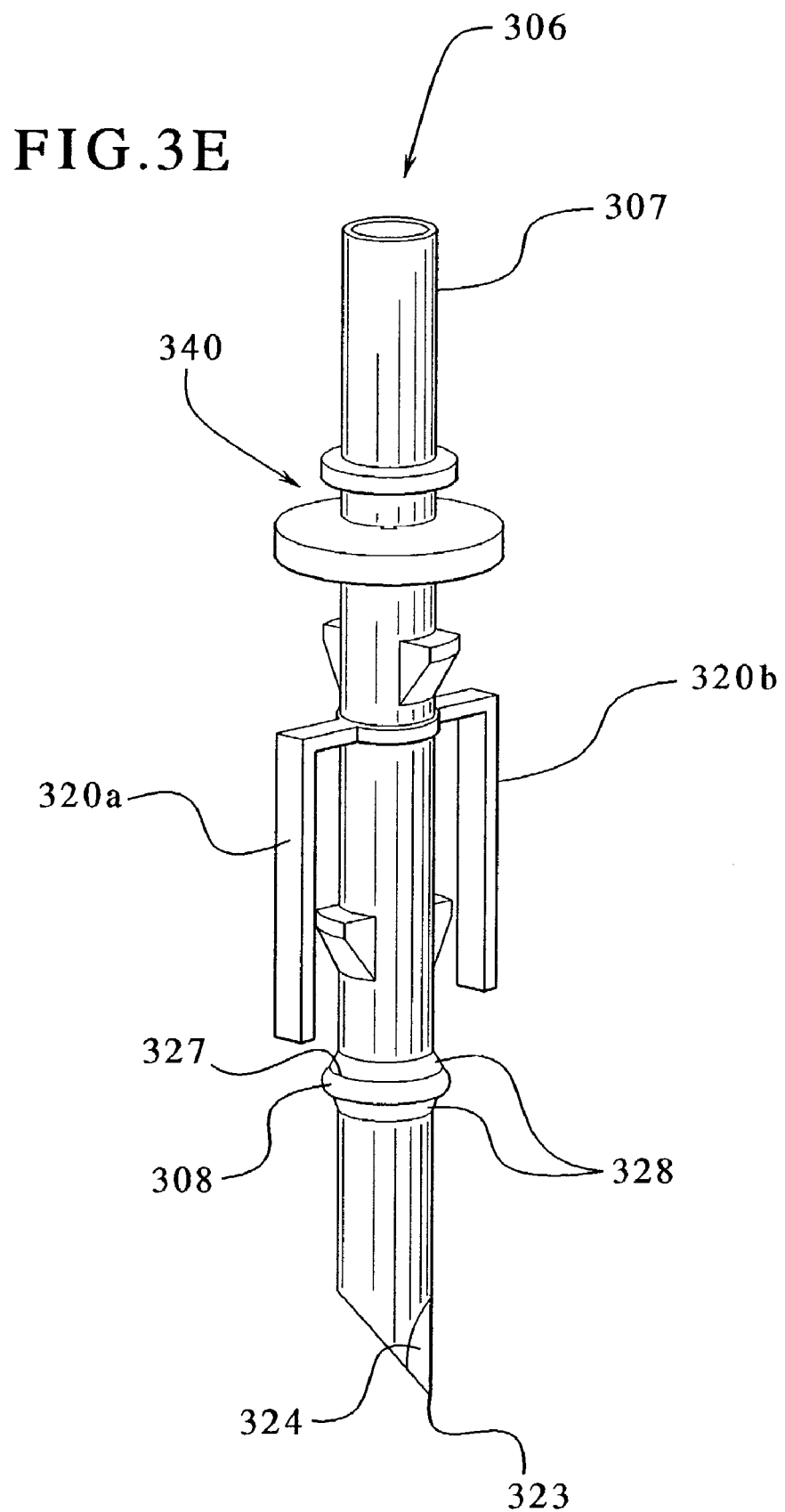
FIG. 3E illustrates a perspective view of a perforator of an access port in an embodiment of the present invention.

Referring to FIG. 3C, the two cantilever beams 314a and 314b, in an open position as shown, may hold the perforator 306 in a standby position. Fourth, the valve 302 may allow for a perforator guiding system. Two slots 318a and 318b are provided to receive arms 320a and 320b of the perforator 306. The arms 320a and 320b are shown in FIGS. 3C, 3D and 3E. The slots 318a and 318b may prevent rotation of the perforator 306 in the valve 302. Fifth, the valve 302 may have threads 319 to guide and/or mate with the threaded shell 304. Finally, as shown in FIG. 3C, the perforator 306 may have two tabs 321 located that secure the assembly in an activated position. The two tabs 322 on the valve 302 impede the rotation of the threaded shell 304 (see FIG. 3A) either in the stand-by position or during the translation of the perforator 306 to an activated position, as shown in FIG. 3D.

Referring to FIG. 3E, the perforator 306 may be molded from, for example, a blend E modulus greater than 1500 MPa. The perforator 306 may have at least five functions. First, the perforator 306 may puncture the film 150 of the container 100 and may establish access to solution in the container 100. A tip 323 of the perforator 306 may have a tri-slope bevel 324. The tri-slope bevel 324 may puncture and/or may tear the film 150 under the peripheral foot section 326 of the valve 302. Further, the tri-slope bevel 324 may generate minimal friction forces.

Second, the perforator 306 may connect the container 100 to the administration line 140. The perforator 306 may have a press fit shaft 307 to press fit and/or bond the administration line 140. The perforator 306 may be hollow. After piercing the film 150, the perforator 306 may generate the fluid path from the container 100 to the administration line 140.

Third, the perforator 306 may have axial and external beams, or cantilever beams, or the arms 320a and 320b that lock into slots 318a and 318b of the valve 302 and may impede any rotation of the perforator 306 during activation. Fourth, the perforator 306 may have a gasket groove 327, the gasket 308 and a guiding flange 328. The gasket groove 327 and the guiding flange 328, in conjunction with the cylindrical hollow shaft 312 in the valve 302, may guaranty the axial guiding and the liquid-tightness of the assembly.

Fifth, the perforator 306 may have a snap 340 that may mate the threaded shell 304 with the valve 302 in an axial position that is substantially fixed but may allow for a rotational degree of freedom. Further, the gasket 308 may ensure the liquid-tightness of the assembly and may prevent any contamination from entering the sterile fluid path.

Figure 3F:
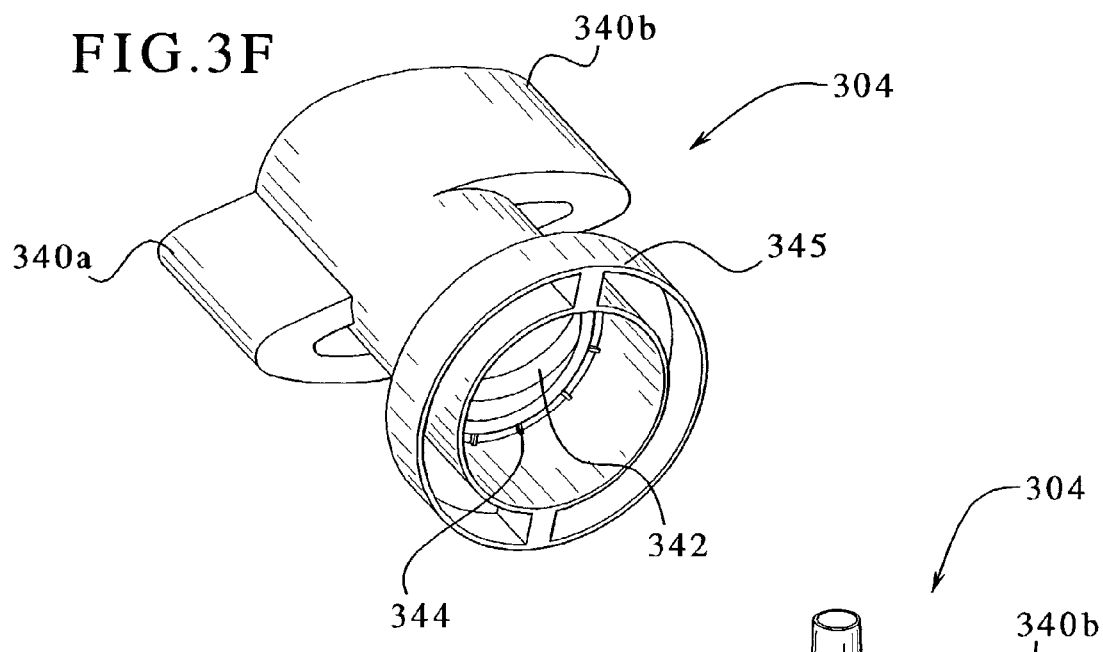
FIG. 3F illustrates a perspective view of a shell of an access port in an embodiment of the present invention.
Figure 3G:
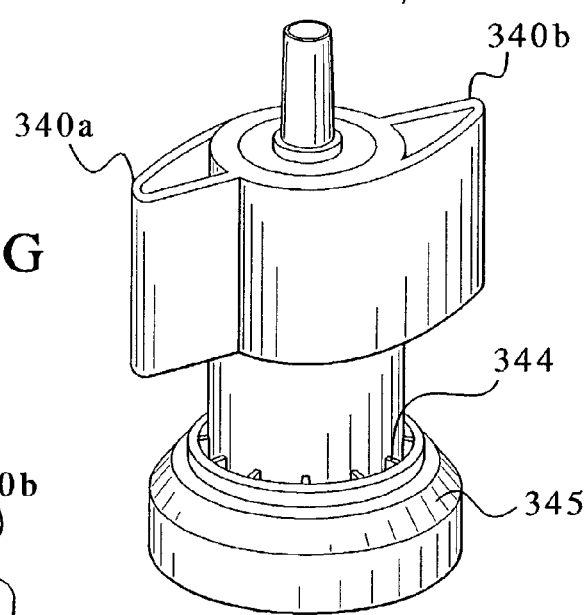
FIG. 3G illustrates a perspective view of a shell of an access port in an embodiment of the present invention.
Figure 3H:
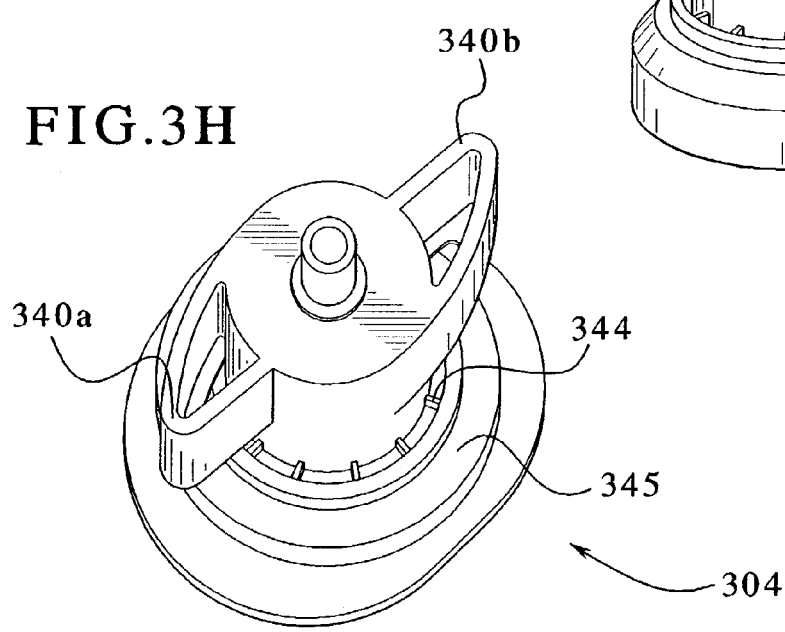
FIG. 3H illustrates a perspective view of a shell of an access port in an embodiment of the present invention.

Referring to FIGS. 3F, 3G and 3H, the threaded shell 304 may be molded from, for example, a blend E modulus around 1000 MPa. The threaded shell 304 may have at least three functions. First, the threaded shell 304 may reduce the forces required to pierce the film 150 of the solution container 100 by providing the two threaded wings 340a and 340b. The fingers and/or hands of a user may be positioned on the threaded wings 340a and 340b. Second, the threaded shell 304 may activate the perforator 306 during rotation by engaging internally built threads 342 in the threaded shell 304 with the threads on the valve 302.

Third, the threaded shell 304 may have a crown 345 removably attached to the threaded shell 304 wherein the crown 345 may provide evidence of tampering. More specifically, in the standby position, as shown in FIG. 3A, the crown 345 of the threaded shell 304 is located on the upper surface of the valve 302 and may be connected to the main body of the threaded shell 304 by breakable sections 344. Initiation of a screwing motion on the threaded shell 304 may tear the breakable sections 344. Broken sections 344 may provide the evidence of tampering. The breakable sections 344 may remain attached to the access port 300 after the crown 345 is detached from the threaded shell 304.

Accordingly, rotating the threaded shell 304 clockwise may tear the breakable sections 344 thereby detaching the protective crown 345. Rotating the threaded shell 304 may engage the valve 302 and the perforator 306. After detaching the protective crown 345, an axial stroke of the perforator 306 may be provided. The axial stroke of the perforator may force the perforator 306 to pierce and become embedded in the container 100. After the perforator 306 pierces the container 100, the access port 300 may be locked in an activated position, and withdrawal of the perforator 306 may not be possible.

The threaded shell 304 may lock onto the valve 302 such that rotation of the threaded shell 304 may be possible but the perforator 306 and the valve 302 may not be disturbed. A reactive force may build in the access port 300 due to the axial stroke of the perforator 306. The reactive force built in the access port 300 may allow for a single-handed operation during the activation of the access port 300.

Figure 4A:
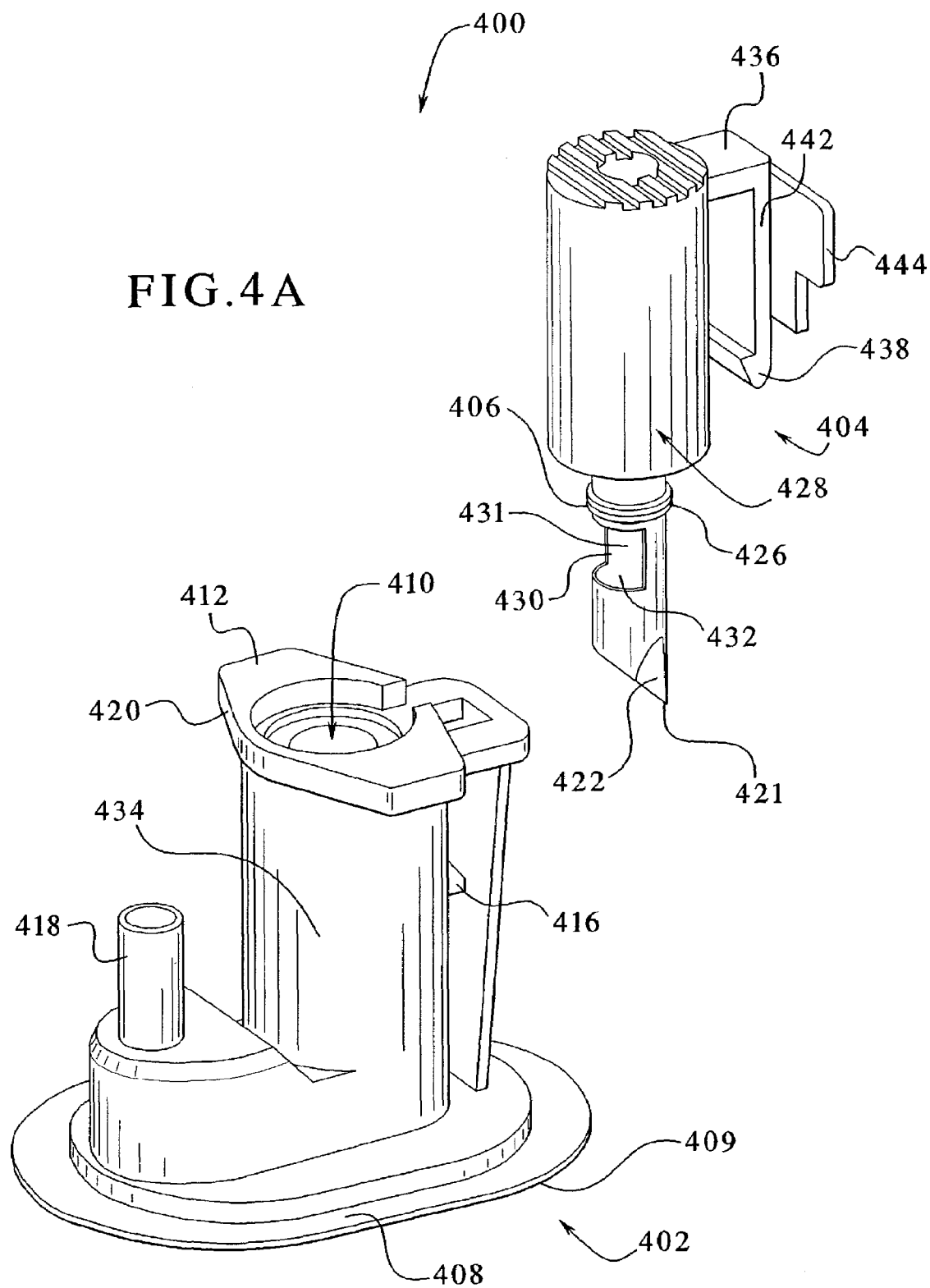
FIG. 4A illustrates a perspective view of a perforator and a valve of an access port in an embodiment of the present invention.

Referring now to FIG. 4A, in another embodiment of the present invention, an access port 400 is generally illustrated. The access port 400 may be constructed from three pieces, namely, a valve 402, a perforator 404, and a gasket 406. The valve 402 may be molded from, for example, a blend E modulus around 900 Mpa. Further, the valve 402 may ensure at least five different functions. First, the valve 402 may have an ability to seal the access port 400 onto the film 150 of the container 100. The valve 402 may have a peripheral section 408 with a thickness 409 and may allow sonic sealing of the peripheral section 408 onto the film 150 of the solution container 100.

Figure 4B:
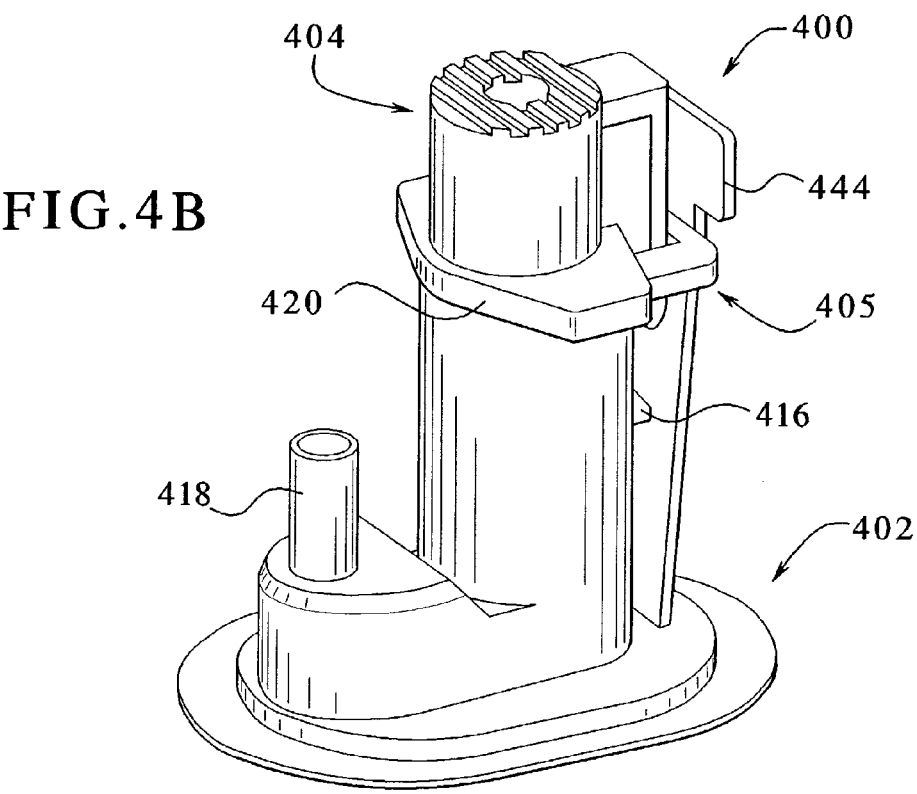
FIG. 4B illustrates a perspective view of an access port in an embodiment of the present invention.
Figure 4C:
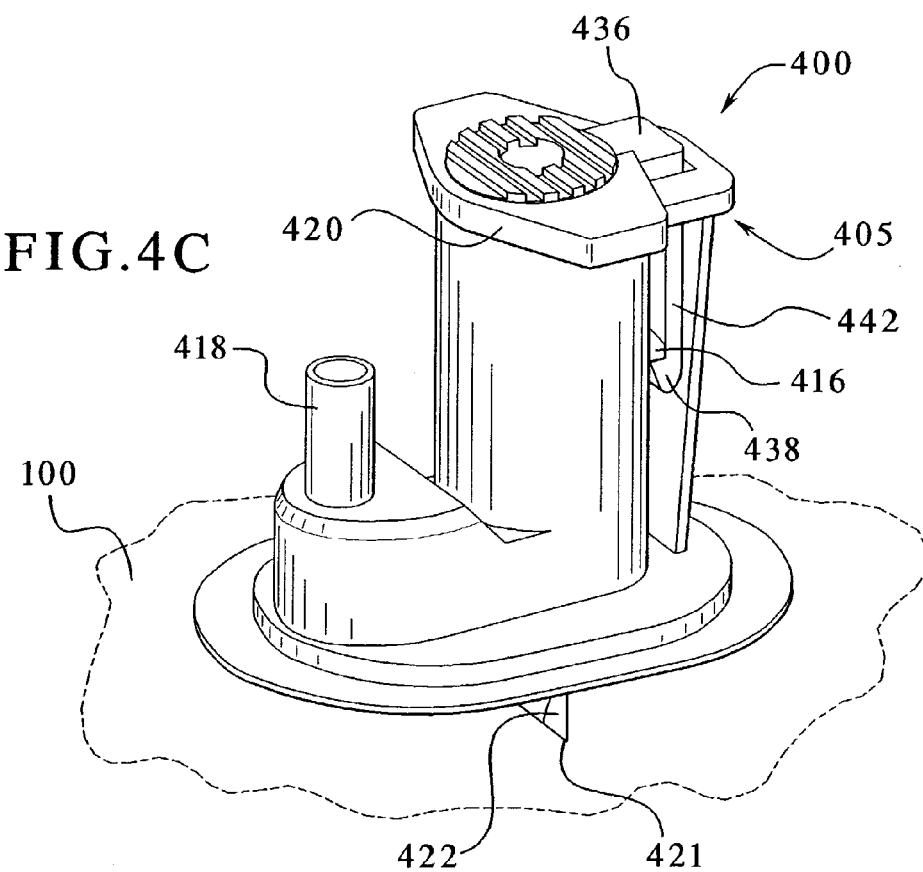
FIG. 4C illustrates a perspective view of an access port in an embodiment of the present invention.

Second, the valve 402 may allow axial guiding of the perforator 404. The valve 402 may have a cylindrical hollow shaft 410 which may be surrounded by a crown 412. Third, the valve 402 may have a perforator locking system 405 in both standby and activated positions as shown in FIGS. 4B and 4C, respectively. On an external side of the valve 402, an external latch 416 may be designed to establish the standby position and the activated position. In the activated position, the access port 400 may be locked.

Fourth, the valve 402 may generate the fluid path and may connect the administration line 140 to the container 100. The valve 402 may have a press fit shaft 418 to bond the administration line 140. Finally, the valve 402 may have a finger pad 420 which may indicate where the fingers of a user may be positioned. The finger pad 420 may concentrate forces that may be applied around the valve 402.

The perforator 404 may be molded from, for example, a blend E modulus greater than 1500 MPa and may provide at least six functions. First, the perforator 404 may puncture the film 150 of the container 100 to provide access to the solution in the container 100. A tip 421 of the perforator 404 may have a tri-slope bevel 422. The tri-slope bevel 422 may be designed to puncture and tear the film 150 beneath the peripheral foot section 408 of the valve 402 with minimal friction forces. Second, the perforator 404 may have a gasket groove 426 and a guiding shroud 428. The gasket groove 426, the gasket 406 and the guiding shroud 428, in conjunction with the cylindrical hollow shaft 410 of the valve 402, may provide axial guidance and liquid-tightness of the access port 400. Third, the perforator 404 may include a blunt hollow shaft 430 from the tip 421 through a middle 431 of an axial extension of the perforator 404. Further, a window 432 in the blunt hollow shaft 430 may allow the solution to flow from the container 100 into a main body 434 of the valve 402.

Fourth, the perforator 404 may include an integral cantilever beam 436 with a catch 438 that mates with the external latches 416 designed on the valve 402. Rotation of the shaft 430 of the perforator 404 inside the valve 402 may be prevented. Further, an arm 442 on an external side of the perforator 404 may be designed to establish the perforator 404 in a standby position and an activated position as shown in FIGS. 4B and 4C, respectively. In the activated position, the access port 400 may be locked.

Fifth, the arm 442 may have a tamper proof tab 444 which may lock the perforator in a standby position and may prevent any unintended activation. The tamper proof tab 444, removably attached to the arm 442, may be removed by breaking the attachment between the tab 444 and the arm 442. Finally, the catch 438 and latches 416 of the perforator 404, when snapped together, may generate an audible notification and/or may also impede any further withdrawal of the perforator 404. The gasket 406 may ensure the liquid-tightness of the assembly and/or may prevent any contamination from entering the sterile fluid path.

Removing the tab 444 may allow an axial stroke of the perforator 404. After the perforator 404 is activated, the perforator 404 may be embedded into the valve 402 so that the perforator 404 may be difficult to withdraw. Due to the axial stroke of the perforator 404, reactive forces may build in the access port 400. The reactive forces in the access port 400 may provide for a single-handed operation while activating the connection and may also prevent the need for maintaining an additional container.

Figure 5A:
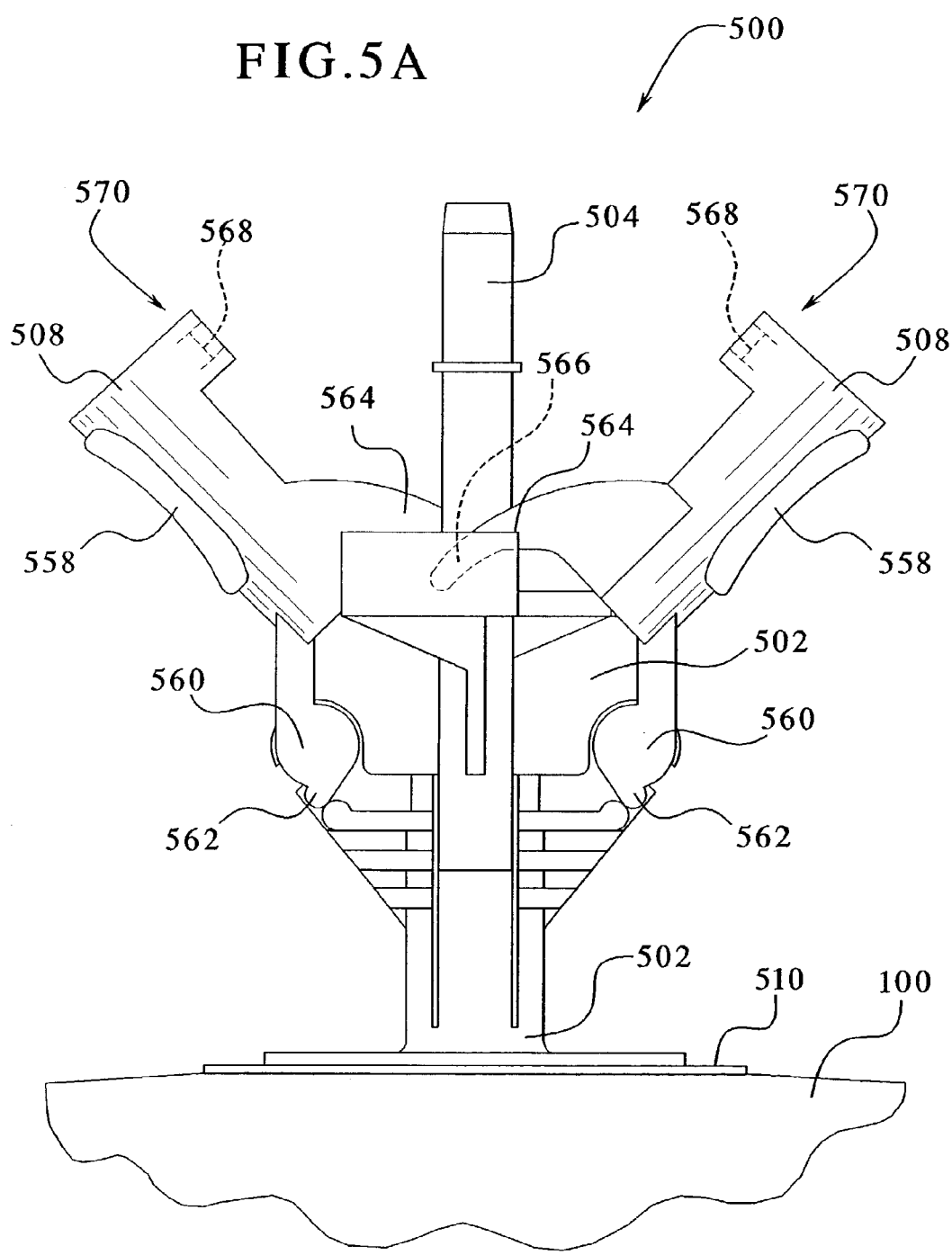
FIG. 5A illustrates a front view of an access port in an embodiment of the present invention.

Referring now to FIG. 5A, in another embodiment of the present invention, an access port 500 is generally illustrated. The access port 500 may be constructed from four components, namely, a valve 502, a perforator 504, a gasket 506, and a shell 508. The perforator 504 of the access port 500 is shown in a standby position.

Figure 5B:
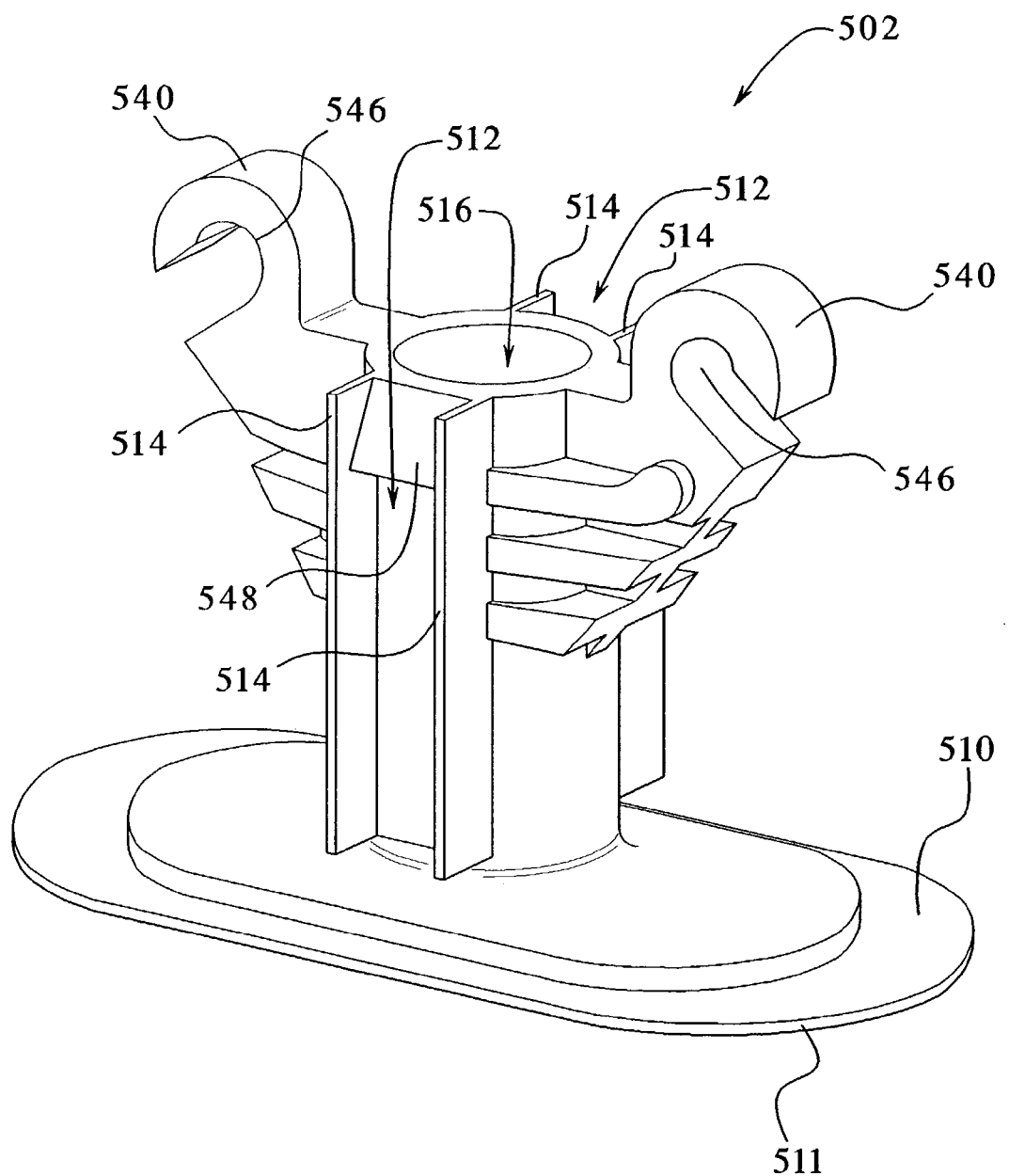
FIG. 5B illustrates a perspective view of a valve of an access port in an embodiment of the present invention.

Referring to FIG. 5B, the valve 502 may be molded from a blend, for example, E modulus around 900 MPa. The valve 502 may have four different functions. First, the valve 502 may seal the access port 500 onto the film 150 of the container 100 as shown in FIG. 5D. The valve 502 may be surrounded by a peripheral foot section 510 having a thickness 511 for sonic sealing of the access port 500 onto the film 150 of the container 100. Second, the valve 502 may axially guide the perforator 504. The valve 502 may provide a cylindrical hollow shaft 516 having four axial and external flanges 514. The axial and external flanges 514 may form two axial sliding slots 516. The axial and external flanges 514 and the axial sliding slots 516 will be discussed in further detail below.

Third, the valve 502 may lock the perforator 504 in both a standby position and an activated position, as shown in FIGS. 5A and 5D, respectively. At extremities of the two axial sliding slots 512, two catches 548 may hold the perforator 504 in the standby position.

Fourth, the valve 502 may attach two shells 508. The valve 502 may have two articulations 540 diametrically opposite and at right angles of the slots 512. The articulations 540 may provide an axis 546 about which the shells 508 may rotate.

Figure 5C:
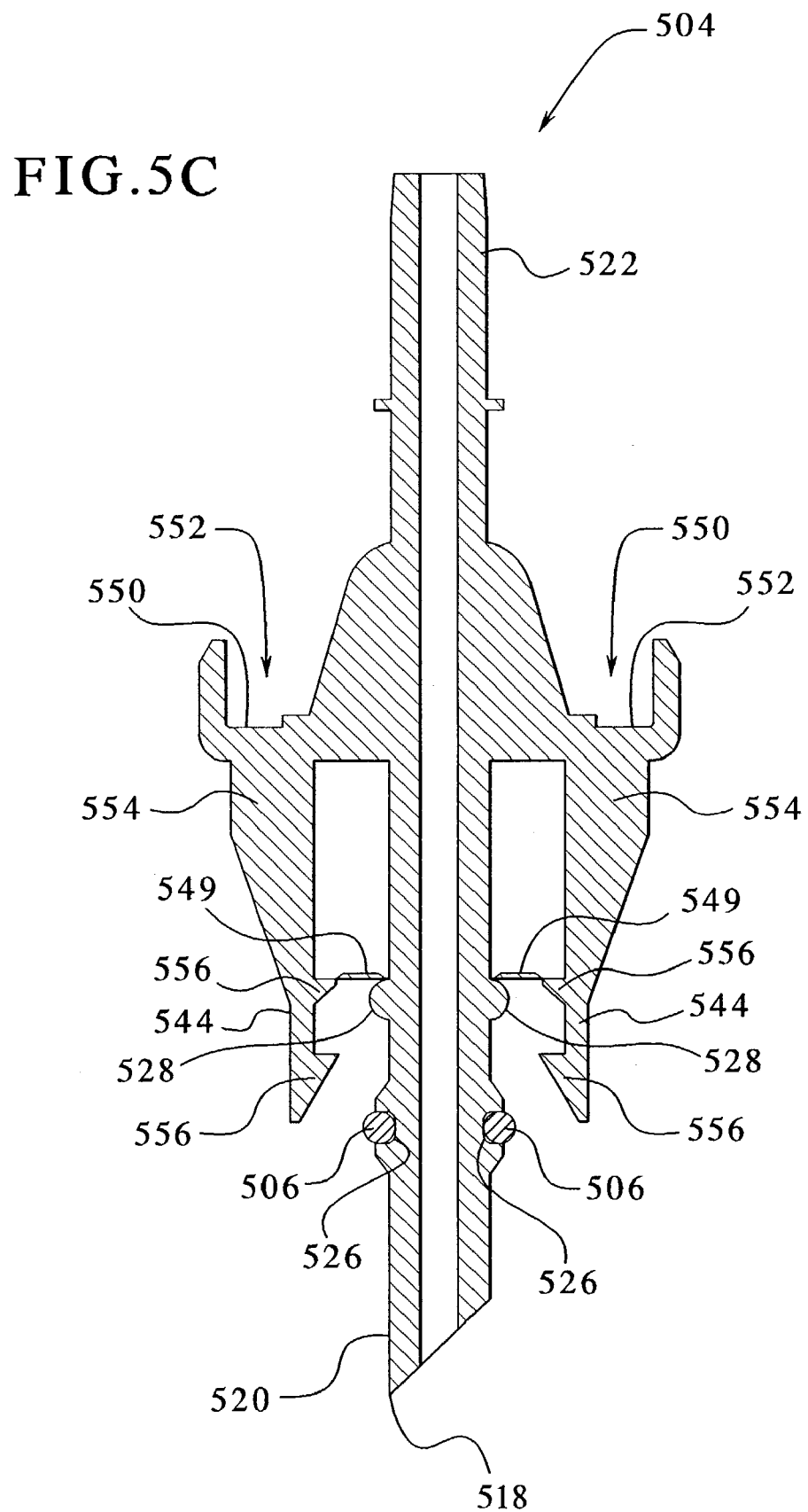
FIG. 5C illustrates a cross-sectional view of a perforator and an O-ring of an access port in an embodiment of the present invention.
Figure 5D:
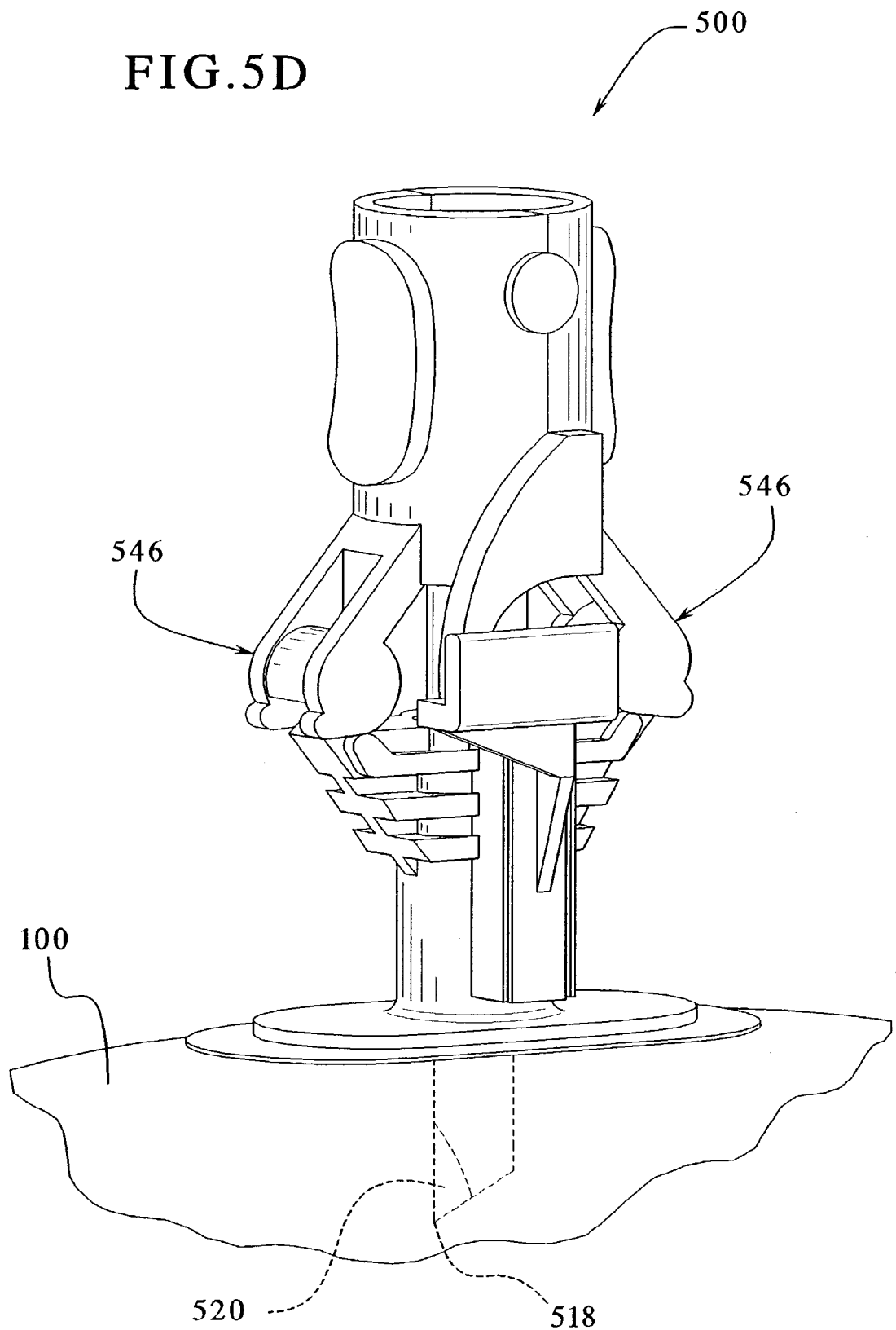
FIG. 5D illustrates a perspective view of an access port in an embodiment of the present invention.

Referring to FIG. 5C, the perforator 504 may be molded from a blend, for example, E modulus >1500 MPA. The perforator 504 provides five functions. First, the perforator 504 may puncture the film 150 of the container 100 and may open an access to the solution of the container 100. A tip 518 of the perforator 504 may have a tri-slope bevel 520 designed to puncture and/or tear the film 150 under the peripheral foot section 510 of the valve 502. The tri-slope bevel 520 of the tip 518 may generate minimal friction forces between the perforator 504 and the film 150.

Second, the perforator 504 may generate a fluid path between the container 100 and another object, such as, for example, a person or second container or the like. Further, the perforator 504 may connect the administration line 140 to the container 100. The perforator 504 is hollow and has a shaft 522 that may be bonded to the administration line 140. Third, the perforator 504 may have a gasket groove 526, a gasket 506 and a guiding flange 528, which, in conjunction with the cylindrical hollow shaft 516 in the valve 502, may guarantee the axial guiding and the liquid-tightness between the perforator 504 and the valve 502. Further, the gasket 506 may ensure the liquid tightness between the perforator 504 and the valve 502 and may prevent contaminants from entering the fluid path from the container 100 to the administrative set.

Fourth, the perforator 504 may have a plateau 550 that may be orthogonal to the axis of the perforator 504. Further, the perforator 504 may have two sliding grooves 552 that transform the pinching motion of the shells 508 into a force directed onto the perforator 504. Fifth, two cantilever beams 554 may mate in slots 512 of the valve 502. The cantilever beams 554, after mating with the slots 512, may prevent the rotation of the perforator 504 inside of the cylindrical hollow shaft 516 of the valve 502. More specifically, catches 548 at the extremities of the slots 512 may lock with latches 556 on the cantilever beams 554. The latches 556 of the cantilever beams 554 may lock the perforator 504 into the standby position and the activated position in the valve 502. The 2 tabs 549 (shown in FIG. 5C) lock-the perforator 504 in stand-by position before use.

Referring again to FIG. 5A, the shell 508 may be molded from a blend, for example, E Modulus>2000 MPa. The shell 508 may provide five functions. First, the shell 508 may provide finger pads 558. When in use, the finger pads 558 may concentrate a pinching force applied by a user. Second, the shell 508 may have an articulation 560 for mating the shell 508 to the valve 502. The articulation 560 may have two protrusions 562 that may block the position of the shell in an angular standby position, as shown in FIG. 5A.

Third, the shell 508 has a beam 564 that rests into the sliding grooves 552 on the plateau 550 of the perforator 504. The beam 564 may transform the force applied by the user into a translation motion. More specifically, a tip 566 of the beam 564 may slide into the sliding grooves 552 of the plateau 550.

Fourth, a latch and catch 568 are provided inside the shell 508 at a distal end 570 of the shell 508. When each shell 508 is snapped together, the catch and latch 568 may lock and generate a sound. The sound may provide an audible notification that the shell 508 is locked. Further, the latch and catch 568, when snapped together, may impede re-opening and/or detaching the shell 508. Fifth, the shell 508, when closed together, may form a cylinder around the activated perforator 504 in such a way that the access port 500 is shrouded as shown in FIG. 5D.

Closing the shell 508 may provide an axial stroke of the perforator 504. Detaching the shell 508 or otherwise moving the shell 508 after the shell 508 has been locked may not move the perforator 504. A ratio of a pivot length may enable the access port 500 to reduce the force required to pierce the film 150 of the container 100. Due to the locking of the shell 508, the reactive force may increase in the access port 500. The reactive force in the access port 500 may provide single-handed operation.

The present invention may provide for a single-handed operation and may provide audible and visible notification when the tri-slope bevel has punctured the film 150 to allow solution flow from the container 100. Further, the present invention may inhibit contamination by fully shrouding the fluid generation path to exclude touch and air-borne contamination and not allowing for the removal of the perforator or plunger from the fluid engagement position, after engagement is achieved. Still further, the present invention may reduce the amount of force needed to penetrate the film of the container.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A container comprising:
   a film folded to define sides wherein the sides are sealed to define an interior;
   a port defining an outlet through which fluid communication with the interior is established, the port comprising;
   a valve affixed to the film, the valve comprising a slot;
   a driver rotatably coupled with the valve;
   a perforator engaged with the driver, the perforator comprising an external beam slideably engaged with the slot of the valve constructed and arranged to impede rotation of the perforator in the valve during activation, the perforator adapted for axial movement within the valve to pierce the film in response to rotation of the driver; and
   a tab releasably attached to the port and impeding rotation of the driver, wherein the tab is configured so that detachment of the tab from the port permits rotation of the driver.

2. The container of claim 1 wherein the tab is attached to the port with a plurality of breakable sections.

3. The container of claim 1 wherein the driver comprises wings.

4. The container of claim 1 wherein rotation of the driver to place the perforator in an activated position produces a sound.

5. The container of claim 1 further comprising: a line having a first end and a second end wherein the first end is attached to the port.

6. The container of claim 1, wherein the perforator further comprises a gasket and a gasket groove.

7. The container of claim 1, wherein the drive comprises an internally threaded shell.

8. The container of claim 7, wherein the perforator comprises a snap that is mateable with the internally threaded shell.

9. The container of claim 7, wherein the valve comprises a tab to impede rotation of the internally threaded shell.

10. The container of claim 9, wherein the tab comprises a crown removably attached to the internally threaded shell.

11. The container of claim 1, wherein the perforator comprises a tip having a tri-slope bevel.

12. The container of claim 1, wherein the perforator is hollow.

13. The container of claim 12, wherein the perforator comprises a press fit shaft attachable to an administration line.

14. The container of claim 1, wherein the valve comprises a cantilever beam and the perforator comprises a tab attachable to the cantilever beam of the valve to securely lock the perforator on the valve in an activated position.

15. The container of claim 1, wherein the valve comprises a peripheral foot section that is sealed onto the film of the container.

* * * * *

UNITED STATES PATENT AND TRADEMARK OFFICE
CERTIFICATE OF CORRECTION

PATENT NO.       : 7,544,191 B2  
APPLICATION NO.  : 10/277432  
DATED            : June 9, 2009  
INVENTOR(S)      : Peluso et al.

Page 1 of 1

It is certified that error appears in the above-identified patent and that said Letters Patent is hereby corrected as shown below:

ON THE TITLE PAGE, ITEM [75]  
Correct "Inventor Giorgio Cantoni, Valdisotto, (IT)" as the country  
Correct "Inventor Silvano Sforacchi, Grosotto (IT)" as the country Signed and Sealed this Fourth Day of August, 2009

JOHN DOLL  
*Acting Director of the United States Patent and Trademark Office*